(12) United States Patent
Ninomiya et al.

(10) Patent No.: US 8,137,941 B2
(45) Date of Patent: Mar. 20, 2012

(54) CHONDROITIN POLYMERASE AND DNA ENCODING THE SAME

(75) Inventors: Toshio Ninomiya, Tokyo (JP); Nobuo Sugiura, Gifu (JP); Koji Kimata, Aichi (JP)

(73) Assignee: Seikagaku Corporation, Tokyo (JP)

( * ) Notice: Subject to any disclaimer, the term of this patent is extended or adjusted under 35 U.S.C. 154(b) by 101 days.

(21) Appl. No.: 12/538,709

(22) Filed: Aug. 10, 2009

(65) Prior Publication Data

US 2009/0305357 A1    Dec. 10, 2009

Related U.S. Application Data

(62) Division of application No. 10/216,289, filed on Aug. 12, 2002, now Pat. No. 7,598,068.

(30) Foreign Application Priority Data

| Aug. 10, 2001 | (JP) | 2001-244685 |
| Oct. 22, 2001 | (JP) | 2001-324127 |
| Apr. 5, 2002 | (JP) | 2002-103136 |

(51) Int. Cl.
*C12P 7/58* (2006.01)
*C12N 9/24* (2006.01)

(52) U.S. Cl. ........ 435/137; 435/200; 435/183; 435/190; 435/193

(58) Field of Classification Search .................. None
See application file for complete search history.

(56) References Cited

FOREIGN PATENT DOCUMENTS

| EP | 1 420 067 A1 | 5/2004 |
| WO | WO 00/27437 | 5/2000 |
| WO | WO 01/80810 | 11/2001 |

OTHER PUBLICATIONS

T. Uyama, et al., The Journal of Biological Chemistry, vol. 277, No. 11, pp. 8841-8846, "Molecular Cloning and Expression of Human Chondroitin *N*-Acetylgalactosaminyltransferase", 2002.

H. Kitagawa, et al., The Journal of Biological Chemistry, vol. 276, No. 42, pp. 38721-38726, "Molecular Cloning and Expression of Human Chondroitin Synthase", 2001.

P. L. Deangelis, et al., The Journal of Biological Chemistry, vol. 275, No. 31, pp. 24124-24129, "Identification and Molecular Cloning OA Chondroitin Synthase From *Pasteurella mulitocida* Type F", 2000.

Nago et al., Computational Complexity, Protein Structure Prediction, and the Levinthal Paradox, in the Protein Folding Problem and Tertiary Structure Prediction, 1994, Merz et al., (ed.), Birkhauser, Boston, MA, pp. 433 and 492-495.

C. R. Drake, et al., "Molecular cloning and expression of the genes encoding the *Escherichia coli* K4 capsular polysaccharide, a fructose substitute chondroitin", FEMS Microbiology Letters, vol. 66, 1990, pp. 227-230.

The 1999 Pierce Catalog, pp. 264-268.

B Jann, et al., "Structure and Biosynthesis of the Capsular Antigens of *Escherichia coli* ", Current Topics in Microgiology and Immunology, vol. 150, 1990, pp. 19 to 42.

Nigel Hodson, et al., "Identification That KfiA, a Protein Essential for the Biosynthesis of the *Eschericia coli* K5 Capsular Polysaccharide, is an α-UDP-GicNAc Glycosyltransferase", The Journal of Biological Chemistry, vol. 275, No. 35, Sep. 2000, pp. 27311-27315.

Carlo Pazzani, et al. "Molecular Analysis of Region 1 of the *Escherichia coli* K5 Antigen Gene Cluster: a Region Encoding Proteins Involved in Cell Surface Expression of Capsular Polysaccharide", Journal of Bacteriology, vol. 174, No. 18, Sep. 1993, pp. 5978-5983.

A.N. Smith, et al, "Molecular analysis of the *Escherichia coli* K5 kps locus: identification and characterization of an inner-membrane capsular polysaccharide transport system", Molecular Microbiology, vol. 4, No. 11, 1990, pp. 1863-1869.

Rigg, P. et al., "The localization of KpsC. S and T. and KfiA, C and D proteins involved in the biosynthesis of the *Escherichia coli* K5 capsular polysaccharide: evidence for a membrane-bound complex", Microbiology, vol. 144, 1998, pp. 2905-2914.

Griffiths G. et al., "Characterization of Glycosyltransferase Enzyme from the *Escherichia coli* K5 Capsule Gene Cluster and Identification and Characterization of the Glucuronyl Active Site", The Journal of Biological Chemistry, vol. 273, No. 19, Issue of May 8, 1998, pp. 11752-11757.

*Primary Examiner* — Richard Hutson
(74) *Attorney, Agent, or Firm* — Oblon, Spivak, McClelland, Maier & Neustadt, L.L.P.

(57) ABSTRACT

A chondroitin polymerase having such properties that it transfers GlcUA and GalNAc alternately to a non-reduced terminal of a sugar chain from a GlcUA donor and a GalNAc donor, respectively, and the like; and a process for producing the chondroitin polymerase.

14 Claims, 5 Drawing Sheets

CHONDROITIN POLYMERASE AND DNA ENCODING THE SAME

BACKGROUND OF THE PRESENT INVENTION

1. Field of the Present Invention

The present invention relates to a novel chondroitin polymerase (chondroitin synthase), a DNA encoding the same, a method for producing the chondroitin polymerase, a method for producing a sugar chain having the disaccharide repeating unit of chondroitin, a hybridization probe for the chondroitin polymerase and the like.

2. Brief Description of the Background Art

First, abbreviations commonly used in the present specification are described.

In the formulae and the like, "GlcUA", "GalNAc", "GlcNAc", "UDP" and "-" represent D-glucuronic acid, N-acetyl-D-galactosamine, N-acetyl-D-glucosamine, uridine 5'-diphosphate and a glycosidic linkage, respectively.

Chondroitin is a sugar chain comprised of a disaccharide repeating structure of GlcUA residue and GalNAc residue (-GlcUAβ(1-3)-GalNAcβ(1-4)-; hereinafter also referred to as "chondroitin backbone"), and a sugar chain in which the chondroitin is further sulfated is chondroitin sulfate.

Regarding an enzyme which synthesizes chondroitin from a GlcUA donor and a GalNAc donor by alternately transferring GlcUA and GalNAc to an acceptor (chondroitin polymerase or chondroitin synthase) and DNA which encodes the same, only a *Pasteurella multocida* chondroitin synthase (*J. Biol. Chem.*, 275 (31), 24124-24129 (2000)) is known.

Also, certain *Escherichia coli* strain (*Escherichia coli* serotype 05:K4 (L):H4, hereinafter referred to as "*Escherichia coli* strain K4") produces a polysaccharide having a chondroitin backbone, as a capsular antigen, but its structure is a trisaccharide repeating structure in which fructose is linked to a side chain of the GlcUA residue at the β2-3 position. Accordingly, it was unclear whether the *Escherichia coli* strain K4 really has a chondroitin polymerase as its own capsular antigen synthesizing system.

SUMMARY OF THE INVENTION

An object of the present invention is to provide a novel chondroitin polymerase, a DNA encoding the same, a process for producing the chondroitin polymerase, a process for producing a sugar chain having the disaccharide repeating unit of chondroitin, a hybridization probe for the chondroitin polymerase and the like.

This and other objects of the present invention have been accomplished by a novel chondroitin polymerase having specific properties described below.

DETAILED DESCRIPTION OF THE INVENTION

Figure 1:
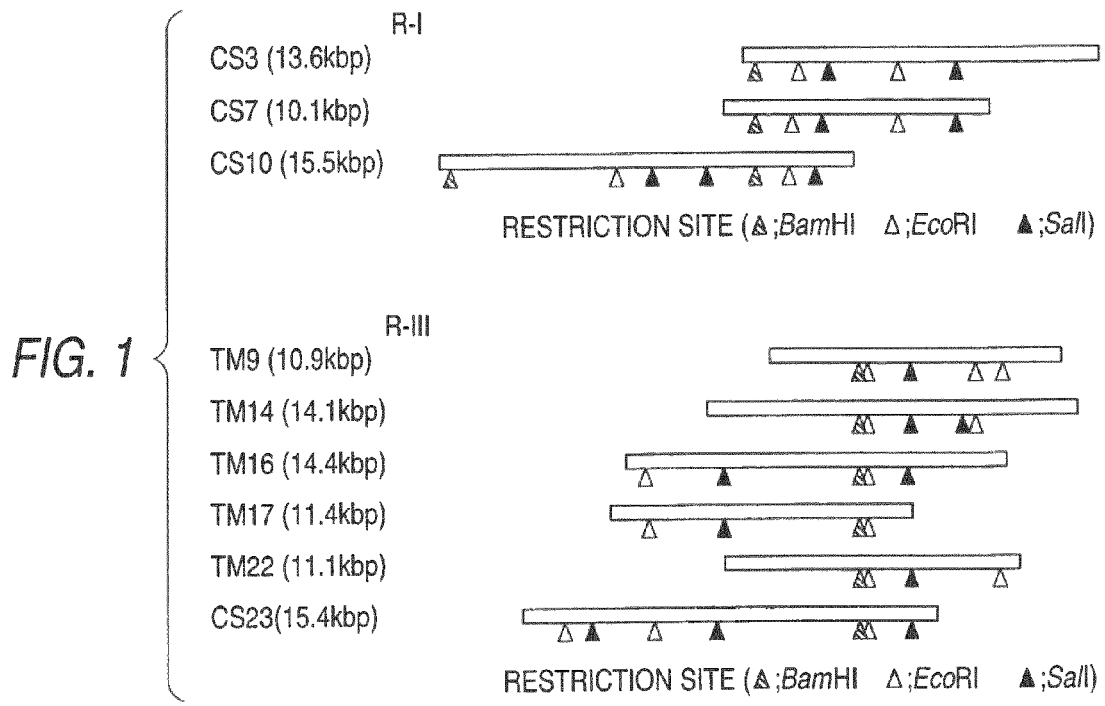
FIG. 1 shows a restriction map of λ phage clones which contain a part of R-I region or R-III region of the K antigen gene cluster of *Escherichia coli* strain K4.

The present inventors have conducted intensive studies and found a novel chondroitin polymerase produced by specific microorganism (*Escherichia coli* strain K4 (*Escherichia coli* serotype 05:K4 (L):H4, ATCC 23502)), isolated cDNA encoding the chondroitin polymerase, and succeeded in preparing the chondroitin polymerase using the cDNA. Thus, the present invention has been completed.

Also, this and other objects of the present invention have been accomplished by a process for producing the chondroitin polymerase by isolating cDNA encoding the chondroitin polymerase and using the cDNA. The term "chondroitin synthesis" or "synthesis of chondroitin" as used herein is a concept which includes elongation of the sugar chain of chondroitin by transferring and adding monosaccharides to a sugar chain such as chondroitin. Accordingly, the reaction for elongating the sugar chain of chondroitin by alternately transferring and adding the chondroitin synthesizing monosaccharides (GlcUA and GalNAc) to the sugar chain is included in a concept of "chondroitin synthesis" or "synthesis of chondroitin".

The present invention relates to a chondroitin polymerase (hereinafter also referred to as "the enzyme of the present invention") having the following properties:

(1) Action:

the polymerase transfers GlcUA and GalNAc alternately to a non-reduced terminal of a sugar chain from, a GlcUA donor and a GalNAc donor, respectively;

(2) Substrate Specificity:

the polymerase transfers GlcUA to an oligosaccharide having GalNAc on its non-reduced terminal and a chondroitin backbone from a GlcUA donor, but does not substantially transfer GalNAc to the oligosaccharide from a GalNAc donor;

the polymerase transfers GalNAc to an oligosaccharide having GlcUA on its non-reduced terminal and a chondroitin backbone from a GalNAc donor, but does not substantially transfer GlcUA to the oligosaccharide from a GlcUA donor;

(3) Influence by Metal Ions and the Like:

the polymerase acts in the presence of $Mn^{2+}$ ion but does not substantially act in the presence of $Ca^{2+}$ ion, $Cu^{2+}$ ion or ethylenediaminetetraacetic acid.

The enzyme of the present invention is preferably derived from *Escherichia coli*.

The present invention relates to a protein selected from the group consisting of the following (A) and (B) (hereinafter also referred to as "the protein of the present invention"):

(A) a protein comprising the amino acid sequence represented by SEQ ID NO:2;

(B) a protein comprising the amino acid sequence in which one or a few amino acid residue(s) in the amino acid sequence represented by SEQ ID NO: 2 are deleted, substituted, inserted or transposed, and having a chondroitin polymerase activity.

The present invention relates to a DNA comprising any one of the following (a) to (c) (hereinafter also referred to as "the DNA of the present invention"):
(a) a DNA which encodes a protein consisting of the amino acid sequence represented by SEQ ID NO: 2;
(b) a DNA which encodes a protein consisting of an amino acid sequence in which one or a few amino acid residue(s) in the amino acid sequence represented by SEQ ID NO: 2 are deleted, substituted, inserted or transposed, and having a chondroitin polymerase activity;
(c) a DNA which hybridizes with
 (i) the DNA in (a),
 (ii) a DNA complementary to the DNA in (a), or
 (iii) a DNA having a part of nucleotide sequences of the DNA in (i) and (ii) under stringent conditions.

The DNA in (a) is preferably represented by SEQ ID NO: 1.

The present invention relates to a vector comprising the DNA of the present invention (hereinafter also referred to as "the vector of the present invention").

The vector of the present invention is preferably an expression vector.

The present invention relates to a transformant in which a host is transformed with the vector of the present invention (hereinafter also referred to as "the transformant of the present invention").

The present invention relates to a process for producing a chondroitin polymerase, which comprises: growing the transformant of the present invention; and collecting the chondroitin polymerase from the grown material (hereinafter also referred to as "the enzyme production process of the present invention").

The present invention relates to a sugar chain synthesizing agent, comprising an enzyme protein which comprises an amino acid sequence represented by the following (A) or (B) and has enzymic activities of the following (i) and (ii) (hereinafter also referred to as "the synthesizing agent of the present invention"):
(A) the amino acid sequence represented by SEQ ID NO:2;
(B) an amino acid sequence in which one or a few amino acid residue(s) in the amino acid sequence represented by SEQ ID NO:2 are deleted, substituted, inserted or transposed;
(i) GlcUA and GalNAc are alternately transferred to a non-reduced terminal of a sugar chain from a GlcUA donor and a GalNAc donor, respectively;
(ii) GlcNAc is transferred to a non-reduced terminal of a sugar chain having GlcUA on the non-reduced terminal from a GlcNAc donor.

The present invention relates to a process for producing a sugar chain represented by the following formula (3), which comprises at least a step of allowing the synthesizing agent of the present invention to contact with a GalNAc donor and a sugar chain represented by the following formula (1) (hereinafter also referred to as "the sugar chain production process 1 of the present invention"):

  (1)

  (3)

wherein X represents GalNAc or GlcNAc; $R^1$ represents an any group; and other symbols have the same meanings as described above.

The present invention relates to a process for producing a sugar chain represented by the following formula (4), which comprises at least a step of allowing the synthesizing agent of the present invention to contact with a GlcNAc donor and a sugar chain represented by the following formula (1) (hereinafter referred to as "the sugar chain production process 2 of the present invention"):

  (1)

  (4)

wherein all symbols have the same meanings as described above.

The present invention relates to a process for producing a sugar chain represented by the following formula (5), which comprises at least a step of allowing the synthesizing agent of the present invention to contact with a GlcUA donor and a sugar chain represented by the following formula (2) (hereinafter also referred to as "the sugar chain production process 3 of the present invention"):

  (2)

  (5)

wherein $R^2$ represents an any group; and other symbols have the same meanings as described above.

The present invention relates to a process for producing a sugar chain selected from the following formulae (6) and (8), which comprises at least a step of allowing the synthesizing agent of the present invention to contact with a GalNAc donor, a GlcUA donor and a sugar chain represented by the following formula (1) (hereinafter also referred to as "the sugar chain production process 4 of the present invention"):

  (1)

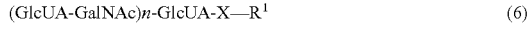  (6)

  (8)

wherein n is an integer of 1 or more, and other symbols have the same meanings as described above.

The present invention relates to a process for producing a sugar chain selected from the following formulae (7) and (9), which comprises at least a step of allowing the synthesizing agent of the present invention to contact with a GalNAc donor, a GlcUA donor and a sugar chain represented by the following formula (2) (hereinafter also referred to as "the sugar chain production process 5 of the present invention"):

  (2)

  (7)

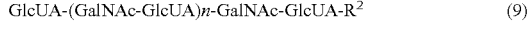  (9)

wherein all symbols have the same meanings as described above.

The present invention relates to a hybridization probe comprising a nucleotide sequence complementary to the nucleotide sequence represented by SEQ ID NO:1 or a part thereof (hereinafter also referred to as "the probe of the present invention").

The present invention relates to a glycosyltransfer catalyst (hereinafter also referred to as "the catalyst of the present invention") which comprises an enzyme protein comprising an amino acid sequence selected from the following (A) and (B), and is capable of transferring GlcUA, GalNAc and GlcNAc to a non-reduced terminal of a sugar chain from a GlcUA donor, a GalNAc donor and a GlcNAc donor, respectively:

(A) the amino acid sequence represented by SEQ ID NO: 2;
(B) an amino acid sequence in which one or a few amino acid residue(s) in the amino acid sequence represented by SEQ ID NO:2 are deleted, substituted, inserted or transposed.

The present invention is explained below in more detail.

<1> Enzyme of the Present Invention and Protein of the Present Invention

The enzyme of the present invention is a chondroitin polymerase having the following properties (1) to (3).

(1) Action:

The enzyme of the present invention transfers GlcUA and GalNAc alternately to a non-reduced terminal of a sugar chain from a GlcUA donor and a GalNAc donor, respectively.

As the GlcUA donor, a nucleoside diphosphate-GlcUA is preferred, and UDP-GlcUA is particularly preferred. Also, as the GalNAc donor, a nucleoside diphosphate-GalNAc is preferred, and UDP-GalNAc is particularly preferred.

The enzyme of the present invention transfers GlcUA and GalNAc alternately to a non-reduced terminal of a sugar chain (acceptor) from these respective saccharide donors. For example, when GlcUA is first transferred to a non-reduced terminal of a sugar chain (acceptor), monosaccharides are transferred in such a manner that GalNAc is then transferred, GlcUA is then transferred, GalNAc is then transferred and so on. In the same manner, when GalNAc is first transferred to the non-reduced terminal of a sugar chain (acceptor), monosaccharides are transferred in such a manner that GlcUA is then transferred, GalNAc is then transferred, GlcUA is then transferred and so on. As a result, a disaccharide repeating structure of GlcUA residue and GalNAc residue, namely a chondroitin backbone, is synthesized by the enzyme of the present invention.

As the sugar chain which becomes the acceptor of monosaccharides, a sugar chain having a chondroitin backbone is preferable. As the sugar chain having a chondroitin backbone, chondroitin sulfate and chondroitin can be exemplified. Among chondroitin sulfates, a chondroitin sulfate which is mainly comprising a chondroitin 6-sulfate structure and also contains a small amount of chondroitin 4-sulfate structure (hereinafter referred to as "chondroitin sulfate C") is preferable.

Also, the sugar chain which becomes an acceptor is more preferably an oligosaccharide. The size of the oligosaccharide is not particularly limited, but when the acceptor is an oligosaccharide of chondroitin sulfate C, hexasaccharide or heptasaccharide is preferable, and tetra-saccharide or hexasaccharide is preferable when it is an oligosaccharide of chondroitin.

Also, it is preferable that the enzyme of the present invention is capable of further transferring GalNAc to a sugar chain having a hyaluronic acid backbone (a disaccharide repeating structure of GlcUA residue and GlcNAc residue) from a GalNAc donor. It is preferable that the sugar chain having a hyaluronic acid backbone is also an oligosaccharide. The size of the oligosaccharide is not particularly limited, but those which are composed of about hexasaccharides are particularly preferable.

(2) Substrate Specificity:

The enzyme of the present invention transfers GlcUA to an oligosaccharide having GalNAc on its non-reduced terminal and a chondroitin backbone from a GlcUA donor, but does not substantially transfer GalNAc to the oligosaccharide from a GalNAc donor.

The enzyme of the present invention transfers GalNAc to an oligosaccharide having GlcUA on its non-reduced terminal and a chondroitin backbone from a GalNAc donor, but does not substantially transfer GlcUA to the oligosaccharide from a GlcUA donor.

It is preferable that the enzyme of the present invention which further does not substantially transfer GlcNAc from a GlcNAc donor to an oligosaccharide having GalNAc on its non-reduced terminal and also has a chondroitin backbone. Furthermore, it is preferable that the enzyme of the present invention further transfers GlcNAc from a GlcNAc donor to an oligosaccharide having GlcUA on its non-reduced terminal and also has a chondroitin backbone. However, it is preferable that GlcUA is not substantially transferred from a GlcUA donor to an oligosaccharide produced by the transfer of GlcNAc.

Also, it is preferable that the enzyme of the present invention transfers GalNAc from a GalNAc donor to an oligosaccharide having GlcUA on its non-reduced terminal and also having a hyaluronic acid backbone, but does not substantially transfer GlcUA from a GlcUA donor.

(3) Influence by Metal Ions and the Like:

The enzyme of the present invention acts in the presence of $Mn^{2+}$ ion but does not substantially act in the presence of $Ca^{2+}$ ion, $Cu^{2+}$ ion or ethylenediaminetetraacetic acid.

Also, it is preferable that the enzyme of the present invention further acts in the presence of $Fe^{2+}$ or $Mg^{2+}$ ion. Moreover, it is preferable that the degree of action (enzyme activity) of the enzyme of the present invention in the presence of $Mn^{2+}$ ion is higher than its degree of action (enzyme activity) in the presence of $Fe^{2+}$ or $Mg^{2+}$ ion.

Also, it was observed that when a reaction was carried out using the enzyme of the present invention at a temperature of 25° C. or more, size of the reaction product (chondroitin chain) became small as the reaction temperature increased (cf., Examples shown below). Accordingly, it is considered that enzyme activity of the enzyme of the present invention decreases as the reaction temperature increases at 25° C. or more under the reaction conditions described in the following Examples.

It is preferable that the enzyme of the present invention is derived from *Escherichia coli*. Particularly, *Escherichia coli* strain having a gene related to the production of capsular polysaccharide is preferable, and *Escherichia coli* strain whose capsular antigen (K) is "K4" is more preferable.

As the *Escherichia coli* strain whose capsular antigen serotype is "K4", *Escherichia coli* strain K4 (*Escherichia coli* serotype 05:K4 (L):H4) can be preferably exemplified, and more specifically, ATCC 23502, NCDC U1-41, Freiburg collection number 2616 and the like can be preferably exemplified.

It is preferable also that the enzyme of the present invention is a protein selected from the following (A) and (B):

(A) a protein comprising the amino acid sequence represented by SEQ ID NO:2;
(B) a protein comprising an amino acid sequence in which one or a few amino acid residue(s) in the amino acid sequence represented by SEQ ID NO: 2 are deleted, substituted, inserted or transposed, and having a chondroitin polymerase activity.

Although mutation such as substitution, deletion, insertion, transposition or the like can occur in amino acid sequences of proteins existing in the nature caused by the modification reactions inside the cells or during purification of proteins after their formation, in addition to polymorphism and mutation of DNA molecules encoding them, it is known that certain proteins having such mutations show physiological and biological activities which are substantially identical to the corresponding proteins having no mutations. Such proteins which have slight structural differences but no significant differences in their functions are also included in the protein of the present invention. A case in which the above mutation is artificially introduced into the amino acid sequence of protein is the same. In such a case, it is possible to prepare larger varieties of mutants. For example, it is known that a polypeptide prepared by substituting a cysteine residue in the amino acid sequence of human interleukin 2 (IL-2) by a serine residue maintains the interleukin 2 activity (*Science*, 224, 1431 (1984)). Also, it is known that a certain protein has a peptide region which is not essential for its activity. For example, a signal peptide existing in a protein which is secreted into the extracellular moiety and a pro-sequence which can be found in a protease precursor or the like correspond to this case, and most of these regions are removed after translation of proteins or during their conversion into active proteins. Such proteins are proteins which are present in different forms in terms of their primary structure but finally have similar functions.

The term "a few amino acid residues" as used herein means the number of amino acids which may cause mutation in such a degree that activity of the chondroitin polymerase is not lost, and in the case of a protein composed of 600 amino acid residues for example, it means the number of approximately from 2 to 30, preferably from 2 to 15, and more preferably from 2 to 8.

Also, the protein of the present invention may contain an amino acid sequence of other protein or peptide, so long as it contains the amino acid sequence of the above (A) or (B). That is, the protein of the present invention may be a fusion protein with other protein or peptide.

For example, fusion proteins of a protein comprising the amino acid sequence described in the above (A) or (B) with a marker peptide and the like are also included in the protein of the present invention. Such proteins of the present invention have a merit in that their purification can be carried out easily. Examples of the above marker peptide include protein A, insulin signal sequence, His, FLAG, CBP (calmodulin-binding protein), GST (glutathione S-transferase) and the like. For example, its fusion protein with protein A can be purified conveniently by affinity chromatography using an IgG-linked solid phase. In the same manner, a solid phase to which magnetic nickel is linked can be used for a fusion protein with His tag, and a solid phase to which an anti-FLAG antibody is linked can be used for a fusion protein with FLAG. Also, since a fusion protein with insulin signal is secreted into an extracellular moiety (a medium or the like), extraction operations such as cell disintegration and the like become unnecessary. It is preferable that the protein of the present invention (the enzyme of the present invention) is soluble.

Preferred examples include a fusion protein with a peptide (His tag) represented by the amino acid sequence represented by SEQ ID NO:11. It is preferable to carry out fusion of this His tag continuously at a position just before the amino acid sequence represented by SEQ ID NO:2. The fusion protein can be produced by expressing a DNA in which the nucleotide sequence represented by SEQ ID NO:4 is connected continuously to a position just before the nucleotide sequence represented by SEQ ID NO:1. The fusion protein is soluble.

The "chondroitin polymerase activity" can be detected in accordance with a generally used glycosyltransferase assay method. Specifically, it can be detected as the activity to synthesize chondroitin by transferring GlcUA and GalNAc alternately to a non-reduced terminal of a sugar chain (acceptor), using a GlcUA donor, a GalNAc donor and a sugar chain which becomes the acceptor.

For example, when GlcUA is transferred from a GlcUA donor to a sugar chain having GalNAc on its non-reduced terminal, and GalNAc is transferred from a GalNAc donor to a sugar chain having GlcUA on its non-reduced terminal, it can be judged that it has an activity to transfer GlcUA and GalNAc alternately to a non-reduced terminal of the sugar chain, namely the chondroitin polymerase activity. It is preferable to employ the enzyme activity measuring method described in the following Examples. By such a method, deletion, substitution, insertion or transposition of amino acids keeping the chondroitin polymerase activity can be selected easily.

Production processes of the enzyme of the present invention and protein of the present invention are not particularly limited, and they can be produced by expressing the DNA of the present invention described below in appropriate cells. Also, those which are isolated from natural resources and produced by chemical synthesis and the like are included in the enzyme of the present invention and the protein of the present invention as a matter of course. The production processes of the enzyme of the present invention (the protein of the present invention) using the DNA of the present invention will be described later.

<2> DNA of the Present Invention

The DNA of the present invention is a DNA comprising any one of the following (a) to (c):
(a) a DNA encoding a protein consisting of the amino acid sequence represented by SEQ ID NO: 2;
(b) a DNA encoding a protein consisting of an amino acid sequence in which one or a few amino acid residue (s) in the amino acid sequence represented by SEQ ID NO: 2 are deleted, substituted, inserted or transposed, and having a chondroitin polymerase activity;
(c) a DNA which hybridizes with the DNA in (a), a DNA complementary to the DNA in (a) or a DNA having a part of nucleotide sequences of the DNA in (i) and (ii) under stringent conditions.

The DNA is preferably represented by SEQ ID NO:1.

The "stringent conditions" as used herein mean conditions under which a so-called specific hybrid is formed but a non-specific hybrid is not formed (cf. Sambrook, J. et al., *Molecular Cloning, A Laboratory Manual*, Second Edition, Cold Spring Harbor Laboratory Press (1989) and the like). Examples of the "stringent conditions" include conditions in which the hybridization is carried out at 42° C. in a solution containing 50% formamide, 4×SSC, 50 mM HEPES (pH 7.0), 10×Denhardt's solution and 100 µg/ml sermon sperm DNA, and the product is washed with 2×SSC, 0.1% SDS solution at room temperature and then with 0.1×SSC, 0.1% SDS solution at 50° C.

The DNA of the present invention is originally obtained from *Escherichia coli* strain having K4 antigen, but DNA samples obtained from other transformed organism species and produced by chemical synthesis and the like are also included therein as a matter of course. Production processes of the DNA of the present invention are not particularly limited too, but it is preferable to use, e.g., the process described in the following Examples.

It is easily understood by those skilled in the art that DNAs having various different nucleotide sequences due to degeneracy of genetic code are present as the DNA of the present invention.

<3> Vector of the Present Invention

The vector of the present invention is a vector comprising the DNA of the present invention. Preferable DNA of the present invention in the vector of the present invention is the same as described in the above <2>. Also, since the vector of the present invention is preferably used in the enzyme production process of the present invention which will be described later, it is preferably an expression vector.

The vector of the present invention can be prepared by inserting the DNA of the present invention into a known vector.

As the vector into which the DNA of the present invention is inserted, for example, an appropriate vector which can express the introduced DNA (a phage vector, plasmid vector or the like) can be used, and it can be optionally selected in response to each host cell into which the vector of the present invention is inserted. Examples of the host-vector system include a combination of a mammal cell such as COS cell, 3 LL-HK46 or the like with an expression vector for mammal cell such as pGIR201 (Kitagawa, H. and Paulson, J. C., *J. Biol. Chem.*, 269, 1394-1401 (1994)), pEF-BOS (Mizushima, S. and Nagata, S. *Nucleic Acid Res.*, 18, 5322 (1990)), pCXN2 (Niwa, H., Yamamura, K. and Miyazaki, J. *Gene,* 108, 193-200 (1991)), pCMV-2 (manufactured by Eastman Kodak), pCEV18, pME18 S (Maruyama et al., *Med. Immunol.,* 20, 27 (1990)), pSVL (manufactured by Pharmacia Biotech) or the like and a combination of *Escherichia coli* with a expression vector for procaryotic cell such as pTrcHis (manufactured by Invitrogen), pGEX (manufactured by Pharmacia Biotech), pTrc99 (manufactured by Pharmacia Biotech), pKK233-3 (manufactured by Pharmacia Biotech), pEZZZ18 (manufactured by Pharmacia Biotech), pCH110 (manufactured by Pharmacia Biotech), pET (manufactured by Stratagene), pBAD (manufactured by Invitrogen), pRSET (manufactured by Invitrogen), pSE420 (manufactured by Invitrogen) or the like. Additionally, an insect cell, yeast, *Bacillus subtilis* and the like can also be exemplified as the host cell and various vectors corresponding thereto can be exemplified. Among the above host-vector systems, a combination of *Escherichia coli* with pTrcHis is preferable.

Also, as the vector into which the DNA of the present invention is inserted, a vector constructed in such a manner that it expresses a fusion protein of the protein of the present invention (enzyme of the present invention) with a marker peptide can also be used, which, as described in the above <1>, is particularly preferable when the chondroitin polymerase expressed using the vector of the present invention is purified. Specifically, a vector comprising a His-expressing nucleotide sequence (e.g., the nucleotide sequence represented by SEQ ID NO:4) is preferable.

When any of the above vectors is used, the DNA of the present invention can be connected with the vector after treating both of them with restriction enzymes and the like and optionally carrying out smooth-ending and connection of a cohesive end so that connection of the DNA of the present invention with the vector becomes possible.

As the process for producing the vector of the present invention, for example, the process described in the following Examples can be used and is preferable.

<4> Transformant of the Present Invention

The transformant of the present invention is a transformant in which a host is transformed with the vector of the present invention.

The "host" as used herein may be any host in which recombination by the vector of the present invention can be carried out but is preferably one which can exert function of the DNA of the present invention or a recombinant vector into which the DNA of the present invention is inserted. Examples of the host include animal cells, plant cells and microbial cells are included, and mammal cells such as COS cells (COS-1 cell, COS-7 cells and the like), 3 LL-HK46 cell, etc., *Escherichia coli*, insect cells, yeast, *Bacillus subtilis* and the like. The host can be optionally selected in response to each vector of the present invention, but, for example, when a vector of the present invention prepared based on pTrcHis is used, it is preferable to select *Escherichia coli* strain.

The host can be transformed by the vector of the present invention in the usual way. For example, the host can be transformed by introducing the vector of the present invention into the host by a method using a commercially available transfection reagent, a DEAE-dextran method, electroporation or the like.

The transformant of the present invention obtained in this manner can be used in the enzyme production process of the present invention described below.

<5> Enzyme Production Process of the Present Invention

The enzyme production process of the present invention is a process for producing a chondroitin polymerase, comprising growing the transformant of the present invention; and collecting a chondroitin polymerase from the grown material.

The term "growing" as used herein means a general idea which includes growth of cells or microorganism as the transformant of the present invention itself and growth of an animal, insect or the like into which cells as the transformant of the present invention are incorporated. Also, the term "grown material" as used herein means a concept which includes a medium (supernatant of culture medium) and cultured host cells after growth of the transformant of the present invention, secreted matter, excreted matter and the like.

Growth conditions (medium, culture condition and the like) are appropriately selected based on the host to be used.

According to the enzyme production process of the present invention, various forms of chondroitin polymerase can be produced based on the transformant to be used.

For example, when a transformant transformed with an expression vector constructed for expressing a fusion protein with a marker peptide is grown, a chondroitin polymerase fused with the marker peptide is produced. Specifically, for example, a chondroitin polymerase fused with His tag is produced by growing a transformant transformed with an expression vector constructed for effecting expression of a protein in which the amino acid sequence represented by SEQ ID NO:12 is continuously fused to a position just before the amino acid sequence represented by SEQ ID NO: 2. Particularly, it is preferable to use a transformant transformed with an expression vector constructed by connecting the nucleotide sequence represented by SEQ ID NO: 11 continuously to a position just before the nucleotide sequence represented by SEQ ID NO: 1.

The chondroitin polymerase can be collected from the grown matter by known protein extraction and purification methods based on the form of the produced chondroitin polymerase.

For example, when the chondroitin polymerase is produced in a soluble form secreted into a medium (supernatant of culture medium), the medium may be collected and used directly as the chondroitin polymerase. Also, when the chondroitin polymerase is produced in a soluble form secreted into the cytoplasm or in an insoluble form (membrane binding), the chondroitin polymerase can be extracted by cell disintegration such as a method using a nitrogen cavitation apparatus, homogenization, glass beads mill, sonication, an osmotic shock method, freezing-thawing, etc., surfactant extraction, a combination thereof or the like, and the extract may be used directly as the chondroitin polymerase.

The chondroitin polymerase can be further purified from the media or extracts, which is preferable. The purification may be either imperfect purification (partial purification) or perfect purification, which can be appropriately selected based on, e.g., the object using the chondroitin polymerase, and the like.

Examples of the purification method include salting out by ammonium sulfate, sodium sulfate, etc., centrifugation, dialysis, ultrafiltration, adsorption chromatography, ion exchange chromatography, hydrophobic chromatography, reverse phase chromatography, gel filtration, gel permeation chromatography, affinity chromatography, electrophoresis, a combination thereof and the like.

Production of the chondroitin polymerase can be confirmed by analyzing its amino acid sequence, actions, substrate specificity and the like.

<6> Synthesizing Agent of the Present Invention

The synthesizing agent of the present invention is a sugar chain synthesizing agent, comprising an enzyme protein which comprises an amino acid sequence represented by the following (A) or (B) and has enzymic activities of the following (i) and (ii):
(A) the amino acid sequence represented by SEQ ID NO: 2;
(B) an amino acid sequence in which one or a few two amino acid residue (s) in the amino acid sequence represented by SEQ ID NO:2 are deleted, substituted, inserted or transposed;
(i) GlcUA and GalNAc are alternately transferred to a non-reduced terminal of a sugar chain from a GlcUA donor and a GalNAc donor, respectively;
(ii) GlcNAc is transferred to a non-reduced terminal of a sugar chain having GluUA on the non-reduced terminal from a GlcNAc donor.

As the "enzyme protein which comprises an amino acid sequence represented by the following (A) or (B) and has enzymic activities of the following (i) and (ii)" which is the active ingredient of the synthesizing agent of the present invention, the enzyme of the present invention or the protein of the present invention can be used as such.

The synthesizing agent of the present invention is a result of applying the "GalNAc transferring action", "GlcNAc transferring action" and "GlcUA transferring action" of the enzyme of the present invention and protein of the present invention as a sugar chain synthesizing agent.

The synthesizing agent of the present invention is used for the synthesis of sugar chains. The term "synthesis of sugar chain" or "sugar chain synthesis" as used herein means a concept including elongation of a certain sugar chain by transferring and adding a monosaccharide to the sugar chain. For example, a concept of transferring and adding a monosaccharide such as GlcUA, GalNAc, GlcNAc or the like to a sugar chain such as chondroitin, chondroitin sulfate, hyaluronic acid and the like to elongate the sugar chain is included in the term "sugar chain synthesis" as used herein.

The form of the synthesizing agent of the present invention is not limited, and it may be any one of a solution form, a frozen form, a freeze-dried form and an immobilized enzyme form in which it is linked to a carrier. Also, it may contain other components (e.g., pharmaceutically acceptable carrier, carrier which is acceptable for reagent, etc.), so long as they do not have influence on the activity of chondroitin polymerase.

<7> Sugar Chain Production Process of the Present Invention

The sugar chain production process of the present invention uses the synthesizing agent of the present invention and is divided into the following five methods in response to the sugar donors and acceptor substrates.

(1) Sugar Chain Production Process of the Present Invention 1

A process for producing a sugar chain represented by the following formula (3), which comprises at least a step of allowing the synthesizing agent of the present invention to contact with a GalNAc donor and a sugar chain represented by the following formula (1):

$$\text{GlcUA-X—R}^1 \quad (1)$$

$$\text{GalNAc-GlcUA-X—R}^1 \quad (3)$$

(2) Sugar Chain Production Process of the Present Invention 2

A process for producing a sugar chain represented by the following formula (4), which comprises at least a step of allowing the synthesizing agent of the present invention to contact with a GlcNAc donor and a sugar chain represented by the following formula (1):

$$\text{GlcUA-X—R}^1 \quad (1)$$

$$\text{GlcNAc-GlcUA-X—R}^1 \quad (4)$$

(3) Sugar Chain Production Process of the Present Invention 3

A process for producing a sugar chain represented by the following formula (5), which comprises at least a step of allowing the synthesizing agent of the present invention to contact with a GlcUA donor and a sugar chain represented by the following formula (2):

$$\text{GalNAc-GlcUA-R}^2 \quad (2)$$

$$\text{GlcUA-GalNAc-GlcUA-R}^2 \quad (5)$$

(4) Sugar Chain Production Process of the Present Invention 4

A process for producing a sugar chain selected from the following formulae (6) and (8), which comprises at least a step of allowing the synthesizing agent of the present invention to contact with a GalNAc donor and a GlcUA donor and a sugar chain represented by the following formula (1):

$$\text{GlcUA-X—R}^1 \quad (1)$$

$$\text{(GlcUA-GalNAc)}n\text{-GlcUA-X—R}^1 \quad (6)$$

$$\text{GalNAc-(GlcUA-GalNAc)}n\text{-GlcUA-X—R}^1 \quad (8)$$

(5) Sugar Chain Production Process of the Present Invention 5

A process for producing a sugar chain selected from the following formulae (7) and (9), which comprises at least a step of allowing the synthesizing agent of the present invention to contact with a GalNAc donor, a GlcUA donor and a sugar chain represented by the following formula (2):

$$\text{GalNAc-GlcUA-R}^2 \quad (2)$$

$$\text{(GalNAc-GlcUA)}n\text{-GalNAc-GlcUA-R}^2 \quad (7)$$

$$\text{GlcUA-(GalNAc-GlcUA)}n\text{-GalNAc-GlcUA-R}^2 \quad (9)$$

In each of the formulae, X represents GalNAc or GlcNAc, and $R^1$ and $R^2$ each represents any group. $R^1$ and $R^2$ are the same or different from each other.

Examples of $R^1$ and $R^2$ include a sugar chain having a chondroitin backbone, a sugar chain having a hyaluronic acid backbone and the like.

The sugar chain represented by formula (1) is preferably chondroitin sulfate (particularly chondroitin sulfate C), chondroitin or hyaluronic acid having GlcUA on its non-reduced terminal, or an oligosaccharide thereof.

The sugar chain represented by formula (2) is preferably chondroitin sulfate (particularly chondroitin sulfate C) or chondroitin having GalNAc on its non-reduced terminal, or an oligosaccharide thereof.

As the GalNAc donor, nucleoside diphosphate-GalNAc is preferable, and UDP-GalNAc is particularly preferable. Furthermore, as the GlcNAc donor, nucleoside diphosphate-GlcNAc is preferable, and UDP-GlcNAc is particularly preferable. Moreover, as the GlcUA donor, nucleoside diphosphate-GlcUA is preferable, and UDP-GlcUA is particularly preferable.

The method for carrying out "contact" is not particularly limited, so long as the enzyme reaction is generated by mutual contact of molecules of the enzyme of the present invention (or the protein of the present invention) contained in the synthesizing agent of the present invention, a donor and an acceptor (sugar chain). For example, the contact may be carried out in a solution in which the three components are dissolved. Also, the enzyme reaction can be carried out continuously using an immobilized enzyme in which chondroitin polymerase contained in the synthesizing agent of the present invention is linked to an appropriate solid phase (beads or the like) or a membrane type reactor using ultrafiltration membrane, dialysis membrane or the like. Also, the enzyme reaction can be carried out by linking the acceptor to a solid phase similar to the method described in WO 00/27437. In addition, a bioreactor which regenerate (synthesize) the donor may be used in combination.

In addition, in the above processes (4) and (5), it is not always necessary to contact the GalNAc donor and GlcUA donor simultaneously with the synthesizing agent of the present invention and the sugar chain represented by formula (1) or (2), and the donors may be allowed to contact alternately.

The conditions for carrying out the enzyme reaction is not particularly limited, so long as they are conditions under which the enzyme of the present invention (or the protein of the present invention) can function, but it is preferable to carry out the reaction at around neutral pH (e.g., about pH 7.0 to 7.5), and it is more preferable to carry out the reaction in a buffer having the buffering action under the pH. Also, the temperature in this case is not particularly limited, so long as the activity of the enzyme of the present invention (or the protein of the present invention) is retained, but a temperature of approximately from 25° C. to 30° C. can be exemplified. Also, when there is a substance which increases the activity of the enzyme of the present invention (or the protein of the present invention), the substance may be added. For example, it is preferable to allow $Mn^{2+}$ and the like to coexist. The reaction time can be determined optionally by those skilled in the art in response to the amounts of the synthesizing agent of the present invention, donor and acceptor to be used and other reaction conditions.

Isolation and the like of sugar chain from the formed product can be carried out by known methods.

Also, a sulfated saccharide such as chondroitin sulfate or the like can be produced by using the synthesizing agent of the present invention (chondroitin polymerase) and a sulfotransferase in combination.

For example, a sulfated saccharide such as chondroitin sulfate or the like can be produced by simultaneously carrying out formation of chondroitin and transfer of sulfate group in the above sugar chain production process, by further allowing a sulfate group donor (3'-phosphoadenosine 5'-phosphosulfate (PAPS) or the like) and a sulfotransferase to coexist. The sulfotransferase may be used as an immobilized enzyme by linking it to an appropriate solid phase (beads or the like) similar to the above case or allowed to react continuously using a membrane type reactor using ultrafiltration membrane, dialysis membrane or the like. In this case, a bioreactor which regenerate (synthesize) the sulfate group donor may be used in combination.

The sulfotransferase which can be used herein may be any enzyme which can transfer a sulfate group to chondroitin and can be appropriately selected from known enzymes based on the kind of desired chondroitin sulfate. Also, two or more kinds of sulfotransferase having different sulfate group transferring positions may be used in combination.

Chondroitin 6-O-sulfotransferase (*J. Biol. Chem.*, 275 (28), 21075-21080 (2000)) can be exemplified as the sulfotransferase. However, there is no limitation thereto and other enzymes can also be used.

<8> Probe of the Present Invention

The probe of the present invention is a hybridization probe comprising a nucleotide sequence complementary to the nucleotide sequence represented by SEQ ID NO:1 or a part thereof.

The probe of the present invention can be obtained by preparing an oligonucleotide comprising a nucleotide sequence complementary to the nucleotide sequence represented by SEQ ID NO:1 or a part thereof, and labeling it with a label suitable for hybridization (e.g., radioisotope).

The size of the oligonucleotide is appropriately selected based on conditions and the like of the hybridization using the probe of the present invention.

It is expected that the probe of the present invention becomes a useful tool for examining biological functions of chondroitin sulfate. This is because chondroitin sulfate is broadly expressed and plays an important role in a large number of tissues, particularly in the brain. It is considered that the probe is also useful in searching for the relationship between genes and diseases.

<9> Catalyst of the Present Invention

The catalyst of the present invention is a glycosyltransfer catalyst which comprises an enzyme protein comprising an amino acid sequence selected from the following (A) and (B), and is capable of transferring GlcUA, GalNAc and GlcNAc from a GlcUA donor, a GalNAc donor and a GlcNAc donor, respectively to a non-reduced terminal of a sugar chain:
(A) the amino acid sequence represented by SEQ ID NO:2;
(B) an amino acid sequence in which one or a few amino acid residue(s) in the amino acid sequence represented by SEQ ID NO: 2 are deleted, substituted, inserted or transposed.

As the "enzyme protein comprising an amino acid sequence represented by (A) or (B)" which is the active ingredient of the catalyst of the present invention, the enzyme of the present invention or protein of the present invention can be used as such.

The catalyst of the present invention is a result of applying the "GalNAc transferring action", "GlcNAc transferring action" and "GlcUA transferring action" of the enzyme of the present invention and protein of the present invention as a glycosyltransfer catalyst.

The catalyst of the present invention can be used for transfer of GlcUA, GalNAc or GlcNAc. For example, it can be used for transferring a monosaccharide such as GlcUA, GalNAc, GlcNAc or the like to a non-reduced terminal of a sugar chain such as chondroitin, chondroitin sulfate, hyaluronic acid or the like.

The form of the catalyst of the present invention is not limited, and it may be any one of a solution form, a frozen form, a freeze-dried form and an immobilized enzyme form in which it is linked to a carrier. Also, it may contain other components (e.g., pharmaceutically acceptable carrier, carrier which is acceptable for reagent, etc.), so long as they do not have influence on the transferring activity of GlcUA, GalNAc or GlcNAc.

Since the enzyme of the present invention and the protein of the present invention can transfer GlcUA and GalNAc alternately as a single molecule, they are markedly useful as tools for the large scale production of sugar chain having a chondroitin backbone (chondroitin, chondroitin sulfate and the like), as the active ingredients of the synthesizing agent of the present invention and the catalyst of the present invention, reagents or the like. Also, the DNA of the present invention is markedly useful as a tool for the large scale production of such enzyme of the present invention and protein of the present invention. The vector of the present invention is markedly useful, because it can retain the DNA of the present invention stably and function effectively and efficiently. The transformant of the present invention is also markedly useful, because not only it can retain the vector of the present invention stably and function effectively and efficiently, but also it can be used as such for the large scale production of the enzyme of the present invention and the protein of the present invention. In addition, the enzyme production process of the present invention is markedly useful for the large scale production of the enzyme of the present invention and protein of the present invention. Also, the sugar chain production process of the present invention is markedly useful for the large scale production of sugar chain having the chondroitin backbone (chondroitin, chondroitin sulfate and the like). The synthesizing agent of the present invention and the catalyst of the present invention are markedly useful, because they can be used in the sugar chain production process of the present invention.

Since high quality and uniform chondroitin polymerase can be produced conveniently, quickly and in a large scale by the present invention, low cost products can be provided for the industrial field and therefore the present invention has markedly high availability.

The present invention is explained in detail based on Examples. However, the present invention is not limited thereto.

UDP-[$^{14}$C]GlcUA, UDP-[$^{3}$H]GalNAc and UDP-[$^{14}$C]GlcNAc used in Examples were purchased from NEN Life Sciences. Also, UDP-GlcUA, UDP-GalNAc and UDP-GlcNAc were purchased from Sigma.

EXAMPLE 1

Cloning of Chondroitin Polymerase Gene (1) Preparation of DNA Library

*Escherichia coli* strain K4 (serotype O5:K4 (L):H4, ATCC 23502) was cultured at 37° C. overnight in 50 ml of LB medium. The cells were collected by centrifugation (3,800 rpm, 15 minutes), suspended in 9 ml of 10 mM Tris-HCl (pH 8.0) buffer containing 1 mM ethylenediaminetetraacetic acid (EDTA) (hereinafter referred to as "TE") and then treated at 37° C. for 1 hour by adding 0.5 ml of 10% SDS and 50 µl of proteinase K (20 mg/ml, Boehringer Mannheim). To the suspension, 10 ml of PCI solution (phenol:chloroform:isoamyl alcohol=25:24:1) was added, followed by stirring for 30 minutes, and the resulting mixture was centrifuged (3,800 rpm, 15 minutes) to collect the water layer and the intermediate layer insoluble matter and again centrifuged (10,000 rpm, 30 minutes). The supernatant was recovered and 50 µl of RNase A (20 mg/ml, Sigma) was added thereto for reaction at 37° C. for 1 hour. To the treated solution, 10 ml of PCI solution was added, followed by stirring for 30 minutes, and the resulting mixture was centrifuged (3,800 rpm, 15 minutes) to collect the water layer and again centrifuged (10,000 rpm, 30 minutes). The supernatant was recovered and dialyzed against 2,000 ml of TE at 4° C. overnight, and the thus dialyzed solution (7.5 ml) was used as a chromosomal DNA solution (DNA concentration, 0.9 mg/ml). The thus obtained K4 strain-derived chromosomal DNA solution (120 µl) was digested using a restriction enzyme Sau3 A1 (4 units: NEB) at 37° C. for 30 minutes and then subjected to 0.3% agarose gel electrophoresis, and then the agarose gel corresponding to the DNA of about 7 to 11 kbp was cut out. The gel thus cut out was put into a 1.5 ml capacity tube having a hole on its bottom pricked with a needle and, together with the tube, inserted into a 2 ml capacity tube and centrifuged (8,000 rpm, 1 minute) to break up the gel. Neutralized phenol in an almost the same volume of the gel was added thereto, followed by vigorously stirring and then the resulting mixture was frozen at −80° C. Thirty minutes thereafter, the temperature was returned to room temperature to melt the mixture, followed by centrifugation (13,000 rpm, 5 minutes). The resulting aqueous layer was collected, the same volume of PCI solution was added thereto, followed by stirring, and then the resulting mixture was centrifuged (13,000 rpm, 5 minutes). The aqueous layer was collected, 1/10 volume of 3 M sodium acetate solution and the same volume of 2-propanol were added thereto to precipitate DNA, and the precipitate was then collected by centrifugation (13,000 rpm, 30 minutes). To the thus collected precipitate, 70% ethanol solution was added, followed by centrifugation (13,000 rpm, 5 minutes), and then the resulting precipitate was dissolved by adding 100 µl of TE. In order to concentrate the resulting solution, DNA was precipitated by adding 10 µl of 3 M sodium acetate solution and 300 µl of ethanol and then recovered by centrifugation (13,000 rpm, 20 minutes). To the thus collected precipitate, 70% ethanol solution was added, followed by centrifugation (13,000 rpm, 5 minutes), and the resulting precipitate was dissolved in 4 µl of purified water to obtain a chromosomal DNA fragment solution. The DNA fragment solution (2 µl) was inserted into a λ phage vector (λ EMBL3: STRATAGENE) which had been treated with restriction enzymes (BamHI (80 units: NEB) and EcoRI (80 units: NEB)) and subjected to packaging using a packaging kit (Gigapack III Gold Packaging Extract, STRATAGENE) in accordance with the manufacture's instructions, and then *Escherichia coli* strain (NM539) was infected with the λ phage and propagated to prepare a K4 chromosomal DNA library.

(2) Preparation of Probe

Among 3 regions of the K antigen gene cluster moiety of *Escherichia coli* strain K5 (serotype O10:K5 (L):H4, ATCC 23506) having known sequences (*Mol. Microbiol.*, 17 (4), 611-620 (1995)), while interposing the K antigen polysaccharide-specific region R-II (gene bank accession NO. X77617), a primer set (CS-S 5'-ACCCAACACTGCTACAACCTATATCGG-3' (SEQ ID NO:5); CS-AS 5'-GCGTCTTCACCAATAAATACCCACGAAACT-3' (SEQ ID NO: 6)) to obtain a DNA fragment of about 1 kbp from the 3'-terminal of the R-I region (gene bank accession NO. X74567), and another primer set (TM-S 5'-CGAGAAATACGAACACGCTTTGGTAA-3' (SEQ ID NO:7); TM-AS 5'-ACTCAATTTTCTCTTTCAGCTCTTCTTG-3' (SEQ ID NO:8)) to obtain a DNA fragment of about 1 kbp from the 5'-terminal of the R-III region (gene bank accession NO. X53819) were selected and prepared.

Using the respective primer sets for R-I and R-III and using, as the template, genome DNA fragments of the strain K4 extracted and purified after Sau3 A1 treatment and subsequent agarose gel electrophoresis in the above (1), polymerase chain reaction (PCR) (94° C., 1 min-(94° C., 45 sec-47° C., 30 sec-72° C., 5 min) 30 cycles-72° C., 10 min (for R-I), 94° C., 1 min-(94° C., 45 sec-50° C., 30 sec-72° C., 5 min) 30 cycles-72° C., 10 min (for R-III)) was carried out to obtain K4-derived R-I region 1.3 kbp (K4 RI3) and R-III region 1.0 kbp (K4 RIII5) DNA fragments. Nucleotide sequences of the thus obtained DNA fragments were determined using ABI PRISM 310 Genetic Analyzer (Perkin-Elmer). The homology with the strain K5 DNA at the same genetic positions was 96% and 95%, respectively.

(3) Gene Cloning of K4 R-II Region

Using respective R-I region and R-III region DNA fragments (K4 RI3 and K4 RIII5) as probes, K4 antigen gene clusters were screened from the K4 chromosomal DNA library obtained in the above (1). *Escherichia coli* (strain NM539) culture (30 μl) was infected with the K4 chromosomal DNA library (λ phage 40 μl) (37° C., 15 minutes), 10 ml of top agarose was added thereto, the resulting mixture was spread on LB plate medium contained in five 10×14 cm Petri dishes, followed by culturing at 37° C. for 9.5 hours to form plaques. Two 9×13 cm membranes (Hybond-N+: Amersham Pharmacia Biotech) were prepared for each plate, and the first and second membranes were put on the medium for 1 minute and 3 minutes, respectively. After removing excess moisture, each membrane was soaked for 2 minutes in 0.5 M NaOH solution containing 1.5 M NaCl to carry out denaturation treatment and then soaked for 3 minutes in 1 M Tris-HCl (pH 7.4) containing 1.5 M NaCl to carry out neutralization treatment. After drying, the membrane was baked at 80° C. for 2 hours to prepare a filter. The filter was subjected to pre-hybridization treatment at 65° C. for 1 hour, hybridized with [$^{32}$P]-labeled K4 RI3 at 64° C. overnight (15 hours) in 0.5 M Church phosphate buffer (pH 7.2), 1 mM EDTA and 7% SDS, and then washed three times with 40 mM Church phosphate buffer (pH 7.2) containing 1% SDS (65° C., each for 15 minutes). The filter was dried and then exposed to an X-ray film to thereby obtain 30 positive plaques. The presence of K4 RI3 was confirmed for each of them by PCR, and 7 plaques among them were subjected to the second screening. Next, the filter hybridized with K4 RI3 was boiled in 0.5% SDS solution for 3 minutes to remove K4 RI3 and then dried to be used as a K4 RIII5 hybridization filter. The filter was subjected to pre-hybridization treatment at 65° C. for 1 hour, hybridized with [$^{32}$P]-labeled K4 RIII5 at 64° C. overnight and then washed three times with 40 mM Church phosphate buffer containing 1% SDS. The filter was dried and then exposed to an X-ray film to thereby obtain 29 positive plaques. The presence of K4 RIII5 was confirmed for each of them by PCR, and 18 plaques among them were subjected to the second screening. In the second screening, LB plate medium of φ 9 cm was used, and positive plaques were obtained by the same method of first screening.

After the first and second screening, 4λ phage clones were obtained from the R-I region, and 10 clones from the R-III region. Each of the clones was subjected to enzyme treatment with EcoRI (10 units: NEB), SalI (10 units: NEB) and BamHI (10 units: NEB), each independently or simultaneously in various combinations, and their restriction maps were prepared based on the size of fragments observed by electrophoresis (FIG. 1).

Among these clones, one clone (CS23, insertion region 15.4 kbp) is a DNA clone prepared based on the R-III region probe, but since it also showed a weak reaction with the R-I region probe, 5'-terminal sequence of the insertion region was examined to find a sequence completely coincided with the 3'-end of the R-I region probe. Since both of the DNA fragments of the R-I region and R-III region were contained in the insertion region, the clone was judged as a clone which contains all of the R-II region of the K antigen gene cluster of the strain K4.

(4) Genetic Analysis of K4 R-II Region

Subcloning of the above CS23 clone was carried out to carry out its sequencing. First, each of about 3 kbp and 8 kbp DNA fragments obtained by treating the CS23 clone with EcoRI and 2 kbp, 5 kbp and 7 kbp DNA fragments obtained by treating it with SaIl was ligated with a cloning vector (pBluescript II KS(-)) and integrated into *Escherichia coli* strain (XLI-Blue) to obtain a clone having different direction of insert. By repeating "treatment of multi-cloning sites of the vector with various restriction enzymes-ligation-transformation" on the clone, 22 plasmids having partial DNA fragments of the R-II region were obtained. By carrying out sequencing of the insertion DNA fragments and connecting them, complete gene sequence of the K4 R-II region was determined (SEQ ID NO: 3). SEQ ID NO: 4 depicts the deduced amino acid sequence encoded by polynucleotides 3787 to 5847 of SEQ ID NO: 3.

(5) Identification of Chondroitin Polymerase Gene

Figure 2:
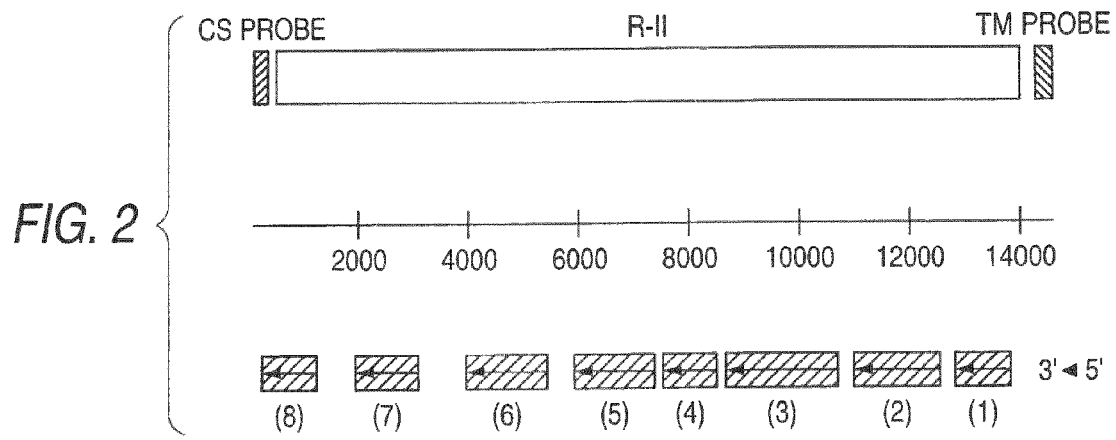
FIG. 2 shows the open reading frame (ORF) of the R-II region of the K antigen gene cluster of *Escherichia coli* strain K4.

As a result of the analysis of the K4 strain R-II region DNA sequence, the presence of 8 open reading frames (ORF) was predicted (FIG. 2).

Among them, the third position ORF counting from the R-III side (2,061 bp (nucleotide numbers 3,787 to 5,847 in SEQ ID NO: 3, sequence of 2,058 bp by excluding the termination codon is shown in SEQ ID NO:1), 686 as the number of amino acids, molecular weight obtained by calculation 79,256 (SEQ ID NO:2)) showed 59% of homology with a *Pasteurella multocida* hyaluronic acid synthase (class 2 type pmHAS; *J. Biol. Chem.*, 273 (14), 8454-8458 (1998)). Also, the first position ORF counting from the R-III side (1,017 bp (nucleotide numbers 643 to 1,659 in SEQ ID NO:3), 339 as the number of amino acids) showed 60% of homology with *Pasteurella multocida* UDP-glucose-4-epimerase (Submitted (29 Oct. 1996) Genetics and Microbiology, Autonomus University of Barcelona, Edifici C, Bellaterra, BCN 08193, Spain), the fourth position ORF (1,332 bp (nucleotide numbers 5,877 to 7,207 in SEQ ID NO:3)) showed high homology (98%) with Insertion Sequence 2 (*Nucleic Acids Res.*, 6(3), 1111-1122 (1979)), and the seventh position ORF (1,167 bp (nucleotide numbers 11,453 to 12,619 in SEQ ID NO:3), 389 as the number of amino acids) showed 65% of homology with the kfiD (*Mol. Microbiol.*, 17(4), 611-620 (1995)) gene (encodes UDP-glucose dehydrogenase) of *Escherichia coli* strain (K5). Also, since the eighth position ORF (1,035 bp (nucleotide numbers 13,054 to 14,088 in SEQ ID NO:3), 345 as the number of amino acids) contained a DXD motif common to glycosyltransferase, it was considered that it has a sugar transferring activity. Regarding the remaining three ORFs (Nos. 2, 5 and 6 (nucleotide numbers 1,849 to 3,486, 7,210 to 8,673 and 9,066 to 10,631, respectively, in SEQ ID NO:3), no homology was found.

EXAMPLE 2

Expression and Enzyme Activity of Chondroitin Polymerase Protein (1) In order to confirm that the K4 R-II region ORF (No. 3) is a chondroitin polymerase gene, primers having restriction enzyme cut sites and interposing the corresponding ORF moiety (K4C-SP 5'-CGGGATCCCGATGAGTATTCT-TAATCAAGC-3' (SEQ ID NO:9); K4C-AS 5'-GGAATTC-CGGCCAGTCTACATGTTTATCAC-3' (SEQ ID NO:10)) were prepared and PCR (94° C., 1 min-(94° C., 30 sec-59° C., 30 sec-74° C., 3 min) 20 cycles-74° C., 10 min) was carried out. The PCR product was subjected to 0.7% agarose gel electrophoresis and extracted and purified using a gel extraction kit (QIAGEN). After treating with restriction enzymes (BamHI and EcoRI), the product was again subjected to 0.7% agarose gel electrophoresis and extracted and purified in the same manner to be used as an insert.

The insert prepared in the above was inserted into an expression vector (pTrcHisC: Invitrogen; containing the nucleotide sequence represented by SEQ ID NO:4) which had been treated with restriction enzymes (BamHI and EcoRI) and CIP, at 16° C. spending 1 hour in the presence of T4 DNA ligase, and transformed into *Escherichia coli* strain (TOP10). By culturing the *Escherichia coli* strain (LB plate medium containing ampicillin, 37° C., overnight), 7 colonies were obtained. One clone containing a plasmid into which the above insert was correctly inserted was selected from them. The *Escherichia coli* was cultured (37° C., overnight) in 1.5 ml of LB medium containing ampicillin (100 µg/ml), and 50 µl of the cultured cell suspension was inoculated into 50 ml of LB medium containing ampicillin (100 µg/ml) and cultured at 37° C. until $OD_{600}$ became 0.6. To the culture, 1 ml of 0.5 M isopropyl 1-thio-β-D-galactoside (IPTG) was added (final concentration: 1 mM) and induction was carried out at 37° C. for 3 hours. The cells were collected by centrifugation (10,000 rpm, 30 minutes) and suspended by adding 4 ml of a lysis buffer (50 mM $NaH_2 PO_4$ (pH 8.0) containing 300 mM NaCl and 10 mM imidazole). To the suspension, 4 mg of lysozyme (Sigma) was added, the resulting mixture was allowed to stand on ice for 30 minutes, and then the cells were disrupted by three times of ultrasonication, each for 10 seconds, using a sonicator. The supernatant was collected by centrifugation (10,000 rpm, 30 minutes) and applied to Ni-NTA agarose column (carrier 1 ml, equilibrated with the lysis buffer; QIAGEN), followed by stirring using a rotor (4° C. for 1 hour). The carrier was sunk by setting up the column and then the column was washed twice using 4 ml for each of a wash buffer (50 mM $NaH_2 PO_4$ (pH 8.0) containing 300 mM NaCl and 20 mM imidazole). Next, proteins were eluted by passing 4 times 0.5 ml for each of an elution buffer (50 mM $NaH_2 PO_4$ (pH 8.0) containing 300 mM NaCl and 250 mM imidazole). The eluate containing the protein of interest (1 ml) was dialyzed at 4° C. for 2 days against 500 ml of PBS (phosphate buffered saline) containing 20% glycerol to thereby obtain about 0.5 ml (protein content 0.4 mg/ml) of dialyzed solution (solution of the enzyme of the present invention (protein of the present invention)).

Western blotting of the thus obtained protein was carried out by sodium dodecyl sulfate-polyacrylamide gel electrophoresis (SDS-PAGE). In the SDA-PAGE, 10% gel was used. Protein was detected by Coomassie Brilliant Blue staining. The Western blotting was carried out by transferring protein in the SDS-PAGE gel onto a nitrocellulose membrane, blocking the membrane with 5% skimmed milk (dissolved in 25 mM Tris-HCl (pH 7.5) containing 150 mM NaCl and 0.05% Tween 20 (this solution is to be called TBS-T)) and then treating it with anti-tetra-His antibody (Qiagen). After washing several times with TBS-T, this membrane was treated with peroxidase-linked anti-mouse IgG. After washing with TBS-T, the reacted protein was detected by ECL detection system (Amersham).

As a result, the protein showed a band at around 80 kDa by the Western blotting analysis using SDS-PAGE and anti-tetra-His antibody. On the other hand, an immunologically reacting band was not detected in the culture extract of a control (expression vector having no insert).

(2) Analysis of Enzyme Activity (Analysis of GalNAc Transfer Activity)

Figure 3:
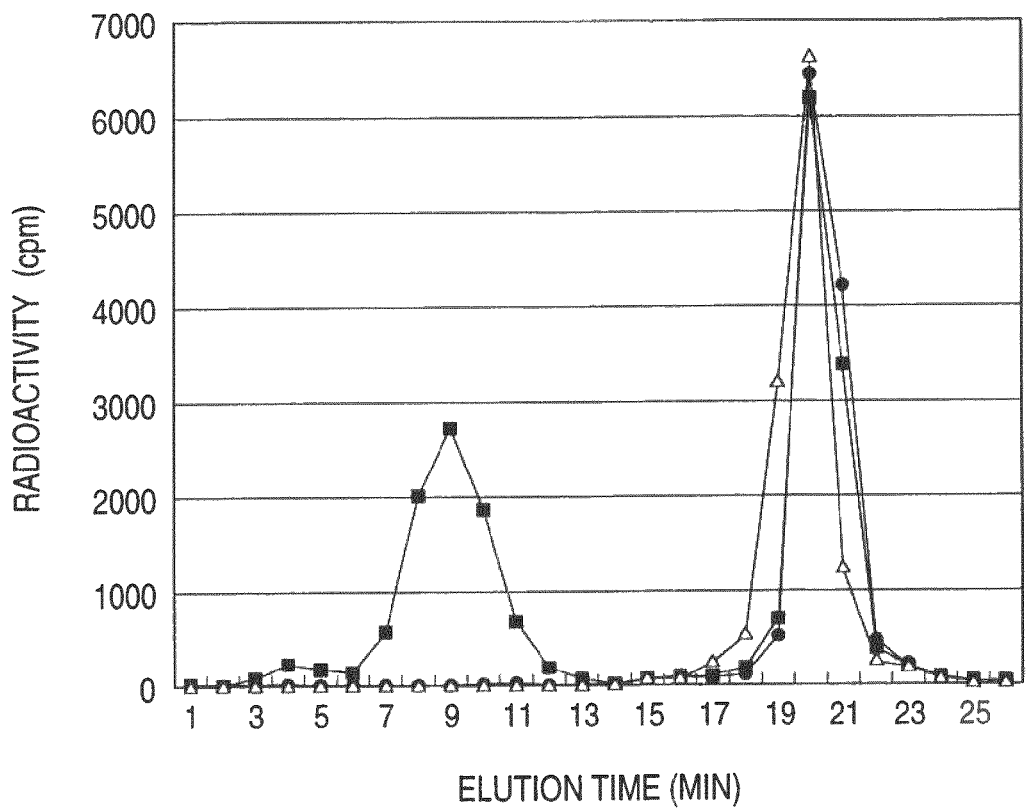
FIG. 3 is a graph showing transfer of GalNAc to hexasaccharide of chondroitin sulfate C by the enzyme of the present invention.

The enzyme of the present invention (2 µg), hexasaccharide of shark cartilage chondroitin sulfate C, purified by degrading with testicular hyaluronidase, as the acceptor (70 pmol) and UDP-GalNAc (3 nmol), UDP-GlcUA (3 nmol) and UDP-[$^3$H]GalNAc (0.1 nmol, 0.1 µCi) as the donors were added to 50 mM Tris-HCl (pH 7.2) containing 20 mM $MnCl_2$, 0.1 M $(NH_4)_2 SO_4$ and 1 M ethylene glycol, and the total volume was adjusted to 50 µl, and then the reaction was carried out at 30° C. for 30 minutes and the enzyme was heat-inactivated. To the reaction solution, 3 volumes of 95% ethanol containing 1.3% potassium acetate was added, and the sample was centrifuged at 10,000×g for 20 minutes. The precipitate was dissolved in 50 µl of distilled water and applied to a Superdex Peptide column (300×φ10 mm: Amersham Biosciences, chromatography conditions; buffer: 0.2 M NaCl, flow rate: 0.5 ml/rain), and the eluate was fractionated at 0.5 ml and the radioactivity (count of [$^3$H]) of each fraction was measured using a scintillation counter. Chondroitin synthesizing activity was determined by calculating the amount of radioactivity incorporated into fractions of higher molecular weight than the acceptor substrate. The results are shown in FIG. 3. In FIG. 3, the closed squares indicate radioactivity when hexasaccharide of chondroitin sulfate C was used as the acceptor, open triangles indicate radioactivity when the enzyme reaction product was treated with chondroitinase ABC and closed circles indicates control (wherein heat-inactivated enzyme of the present invention was used).

As a result, elution position of the radioactivity appeared at a higher molecular weight side than the hexasaccharide of chondroitin sulfate C (the broad peak having its top at around 5,000 Da) (closed squares in FIG. 3). Also, when the enzyme reaction product was treated with chondroitinase ABC, the high molecular weight peak was shifted to a position corresponding to the disaccharide fraction (open triangles in FIG. 3). When disaccharide composition of this chondroitinase ABC digest was analyzed using a high performance liquid chromatography (HPLC), only an un-sulfated, unsaturated chondroitin disaccharide (ΔdiOS) was detected.

Also, the enzyme reaction product was completely digested by chondroitinase ACII treatment too, but not digested by *Streptomyces* hyaluronidase and heparitinase I.

Based on the above, it was shown that the thus obtained enzyme of the present invention at least transfers GalNAc to the hexasaccharide of chondroitin sulfate C from UDP-GalNAc (donor). This specific activity was 3.25±0.64 nmol GalNAc/min/mg protein.

(3) Analysis of Size of Enzyme Reaction Product

The size of the enzyme reaction product was examined by carrying out the enzyme reaction and chromatography in the same manner as in the above "(2) Analysis of enzyme activity". The results are shown in FIG. 4.

Figure 4:
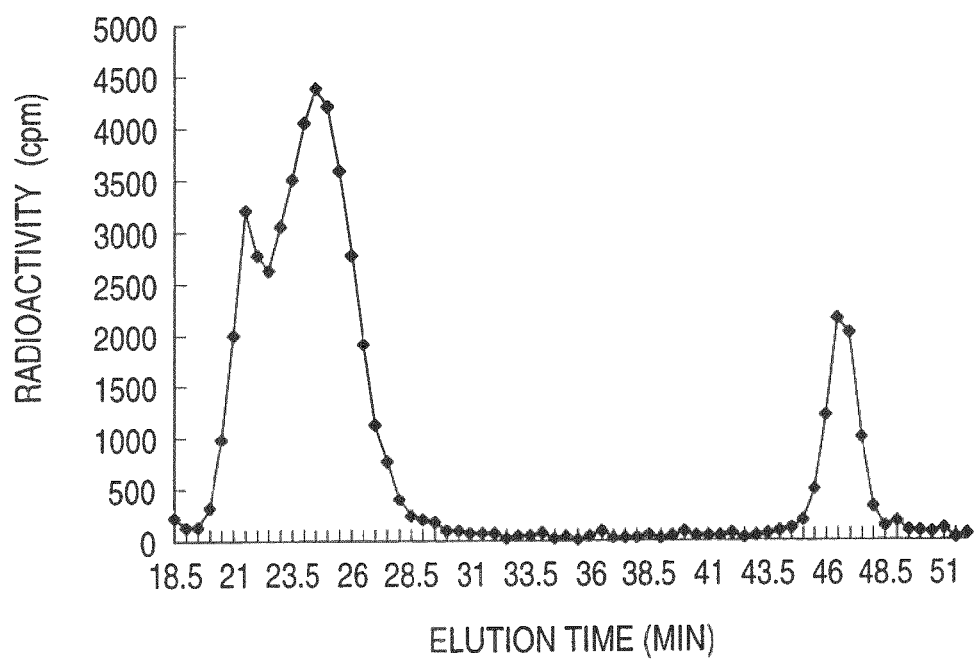
FIG. 4 is a graph showing transfer of GalNAc to hexasaccharide of chondroitin sulfate C by the enzyme of the present invention and the sizes of the produced sugar chain.

It was confirmed from FIG. 4 that the enzyme of the present invention obtained in the above at least transfers GalNAc to an acceptor (an oligosaccharide having the chondroitin backbone (hexasaccharide of chondroitin sulfate C prepared using testicular hyaluronidase)) from a GalNAc donor (UDP-GalNAc) to thereby form chondroitin having a molecular weight of 10,000 to 20,000 or more.

(4) Analysis of Specificity of Donor Substrate

Using UDP-[$^{14}$C]GlcUA, UDP-[$^{14}$C]GlcNAc or UDP-[$^3$H]GalNAc as the donor, transferring activity to the following acceptors was examined in accordance with the method described in the above "(2) Enzyme activity measurement". Products after the enzyme reaction were analyzed by gel filtration.

Figure 5:
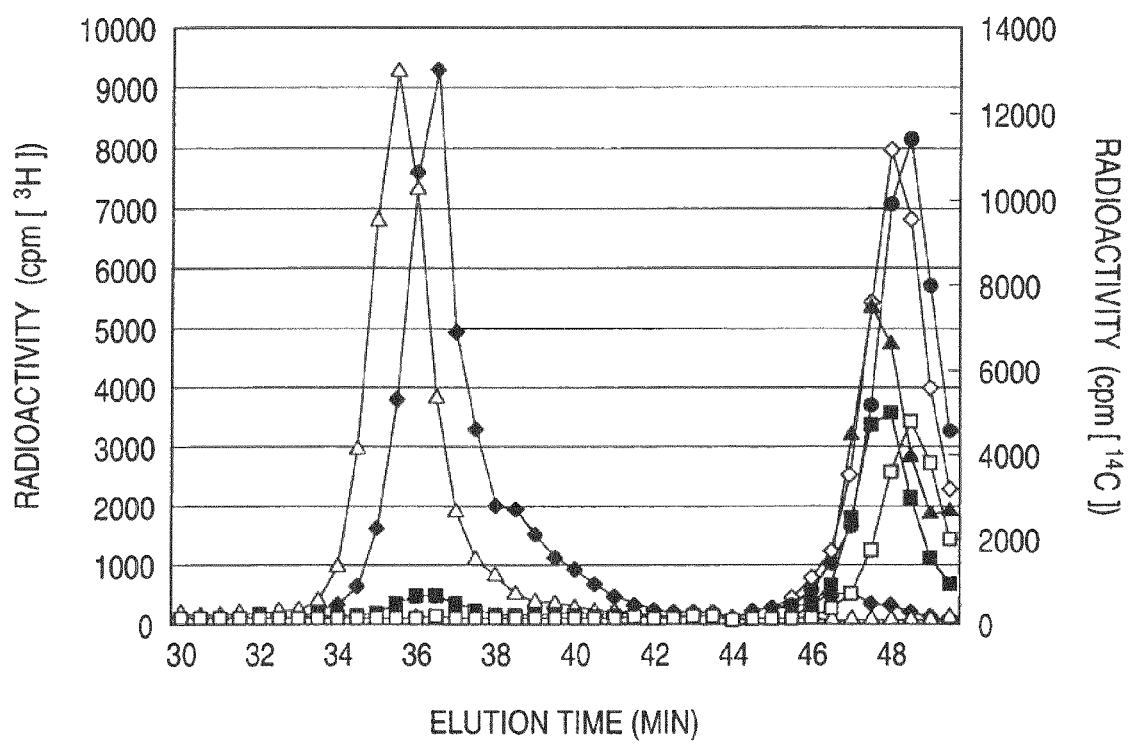
FIG. 5 is a graph showing transfer of each monosaccharide when UDP-GlcUA, UDP-GlcNAc or UDP-GalNAc was used as the donor, and hexasaccharide or heptasaccharide of chondroitin sulfate C was used as the acceptor.

Results of the use of hexasaccharide or heptasaccharide of chondroitin sulfate C as the acceptor are shown in FIG. 5. Also, the closed circle in FIG. 5 indicates a control (a case in which heat-inactivated enzyme of the present invention was used).

(A) Hexasaccharide of chondroitin sulfate C (A product purified by degrading shark cartilage chondroitin sulfate C with testicular hyaluronidase, and the non-reduced terminal is GlcUA)

Heptasaccharide alone was synthesized when UDP-GalNAc alone was used as the donor (closed lozenge in FIG. 5).

Substantial transfer was not found when UDP-GlcUA alone was used as the donor (closed triangle in FIG. 5).

Although very little, transfer of GlcNAc was found when UDP-GlcNAc alone was used as the donor. This transferring activity was 6.3% based on 100% activity in the case of the use of UDP-GalNAc as the donor (closed square in FIG. 5). However, polysaccharides having a size of octasaccharide or more were not obtained even when both of UDP-GlcNAc and UDP-GlcUA were used together with this.

In addition, since incorporation of the radioactivity was not found in the absence of acceptor substrate, it was suggested that an acceptor substrate is essential for the synthesis of chondroitin by this enzyme.

(B) Heptasaccharide of chondroitin sulfate C (A product obtained by allowing the enzyme of the present invention to react with the above hexasaccharide of chondroitin sulfate C and thereby linking one residue of GalNAc to the non-reduced terminal of the hexasaccharide)

Octasaccharide alone was synthesized when UDP-GlcNAc alone was used as the donor (open triangle in FIG. 5).

When either UDP-GalNAc or UDP-GlcNAc alone was used as the donor, substantial transfer was not found in each case (respectively, open lozenge and open square in FIG. 5).

Also, results of carrying out similar tests each independently are shown in Table 1. Also, the term "CS" in Table 1 means chondroitin sulfate C. Also, parenthesis in the table shows length of sugar chain after the enzyme reaction and "-" means that the labeled UDP-sugar was not transferred to the corresponding acceptor substrate.

TABLE 1

| Donor substrate | | Chondroitin polymerase-specific activity (nmol/min/mg protein) Acceptor substrate | |
|---|---|---|---|
| Labeled UDP-sugar | Unlabeled UDP-sugar | CS hexasaccharide | CS heptasaccharide |
| UDP-[$^3$H]GalNAc | none | 0.59 ± 0.16 (hepta) | 0.0 ± 0.0 (—) |
| UDP-[$^{14}$C]GlcNAc | none | 0.04 ± 0.02 (hepta) | 0.0 ± 0.0 (—) |
| UDP-[$^{14}$C]GlcUA | none | 0.0 ± 0.0 (—) | 0.53 ± 0.08 (octa) |
| UDP-[$^3$H]GalNAc | UDP-GlcUA | 3.25 ± 0.64 (poly) | not measured |
| UDP-[$^{14}$C]GlcUA | UDP-GalNAc | 2.75 ± 0.28 (poly) | not measured |
| UDP-[$^{14}$C]GlcNAc | UDP-GlcUA | 0.05 ± 0.02 (poly) | not measured |
| UDP-[$^{14}$C]GlcUA | UDP-GlcNAc | 0.0 ± 0.0 (—) | not measured |

Prom the above results, it was shown that the enzyme of the present invention obtained in the above transfers GalNAc from UDP-GalNAc to a sugar chain (acceptor) having a chondroitin backbone whose non-reduced terminal is GlcUA. Also, it was shown that when the acceptor is used, the enzyme of the present invention obtained in the above shows the activity to transfer GlcNAc from UDP-GlcNAc, but the activity is far lower than its GalNAc transferring activity. Also, it was shown that when the acceptor is used, the enzyme of the present invention obtained in the above does not substantially have the activity to transfer GlcUA from UDP-GlcUA. Based on these results, it was shown that the above enzyme of the present invention is not capable of transferring GlcUA to the non-reduced terminal GlcUA but is capable of transferring one residue of GalNAc (or, though slight, GlcNAc).

Also, it was shown that the enzyme of the present invention obtained in the above transfers GlcUA from UDP-GlcUA to a sugar chain (acceptor) having a chondroitin backbone whose non-reduced terminal is GalNAc. Also, it was shown that when the acceptor is used, the enzyme of the present invention obtained in the above substantially have no activities to transfer GalNAc from UDP-GalNAc and to transfer GlcNAc from UDP-GlcNAc. Based on these results, it was shown that the above enzyme of the present invention is not capable of transferring GalNAc to the non-reduced terminal GalNAc but is capable of transferring one residue of GlcUA.

Based on the above, it was shown that the above enzyme of the present invention is capable of transferring GlcUA and GalNAc alternately from a GlcUA donor and a GalNAc donor, respectively, to the sugar chain non-reduced terminal.

(5) Analysis of Specificity of Acceptor Substrate

Using tetrasaccharide (140 pmol) or hexasaccharide (140 pmol) of chondroitin sulfate C degraded and purified using testicular hyaluronidase, tetrasaccharide (260 pmol) or hexasaccharide (175 pmol) of chondroitin degraded and purified by the Nagasawa's method (*Carbohydrate Research*, 97, 263-278 (1981)), hexasaccharide (175 pmol) of hyaluronic acid degraded and purified using testicular hyaluronidase, chondroitin sulfate C (molecular weight 20,000), chondroitin (molecular weight 10,000), dermatan sulfate (molecular weight 15,000), hyaluronic acid (molecular weight 20,000) or heparin (molecular weight 10,000) as the acceptor, the transferring activity was examined by the following method. Also, the sugar chains were purchased from Seikagaku Corporation.

The enzyme of the present invention (2 μg), UDP-GalNAc (Sigma) (60 pmol), UDP-GlcUA (Sigma) (0.6 nmol) and UDP-[$^3$H]GalNAc (0.1 nmol, 0.1 μCi) as the donors and each of the above sugar chains as the acceptor were added to 50 mM Tris-HCl (pH 7.2) containing 20 mM MnCl$_2$, 0.1 M (NH$_4$)$_2$ SO$_4$ and 1 M ethylene glycol, and the total volume was adjusted to 50 μl, and then the enzyme reaction was carried out at 30° C. for 30 minutes and the enzyme was heat-inactivated. The reaction solution was applied to a Superdex Peptide column (300×ϕ10 mm: Amersham Biosciences, chromatography conditions; buffer: 0.2 M NaCl, flow rate: 0.5 ml/min), and the eluate was fractionated at 0.5 ml and the radioactivity (count of [$^3$H]) of each fraction was measured using a scintillation counter. The results are shown in Table 2. The parenthesized numerals in the table are relative values when the quantity of radioactivity (amount of transferred GalNAc) by the use of the hexasaccharide of chondroitin sulfate C as the acceptor was defined as 100%.

TABLE 2

| Acceptor substrate | | Specific activity of [$^3$H] incorporation | |
|---|---|---|---|
| | | nmol/min/mg protein | % |
| Chondroitin sulfate C | Tetrasaccharide | 1.44 ± 0.24 | 43.0 |
| | Hexasaccharide | 3.34 ± 0.50 | 100.0 |
| | Polysaccharide (M.W. 20,000) | 3.41 ± 0.48 | 100.0 |
| Chondroitin | Tetrasaccharide | 1.12 ± 0.21 | 33.5 |
| | Hexasaccharide | 1.24 ± 0.45 | 37.0 |

TABLE 2-continued

| Acceptor substrate | | Specific activity of [³H] incorporation | |
|---|---|---|---|
| | | nmol/min/mg protein | % |
| | Polysaccharide (M.W. 10,000) | 0.53 ± 0.13 | 15.8 |
| Hyaluronic acid | Hexasaccharide | 0.80 ± 0.15 | 24.0 |
| | Polysaccharide (M.W. 20,000) | 0.27 ± 0.02 | 8.2 |
| Dermatan sulfate | Polysaccharide (M.W. 15,000) | 0.06 ± 0.02 | 1.9 |
| Heparin | Polysaccharide (M.W. 10,000) | 0.0 ± 0.0 | 0.0 |

Based on the above results, it was shown that the hexasaccharide of chondroitin sulfate C becomes the most suitable acceptor substrate. The chondroitin hexasaccharide also functioned as an acceptor substrate, but its activity was low (37%) in comparison with the case of the hexasaccharide of chondroitin sulfate C. Incorporation into the chondroitin sulfate tetrasaccharide or chondroitin tetrasaccharide was the same (43% and 33.5%, respectively). To our surprise, the hyaluronic acid hexasaccharide and hyaluronic acid (molecular weight 20,000) also functioned as acceptor substrates. The incorporation level of chondroitin sulfate C (molecular weight 20,000) was similar to that of the hexasaccharide of chondroitin sulfate C. The incorporation was not so high in the case of chondroitin (molecular weight 10,000).

In summing up the above results, it was shown that the above enzyme of the present invention uses oligosaccharides and polysaccharides having chondroitin backbone (at least tetrasaccharide, hexasaccharide and heptasaccharide of chondroitin sulfate C, chondroitin tetrasaccharide and hexasaccharide, chondroitin sulfate C (molecular weight 20,000) and chondroitin (molecular weight 10,000)) and oligosaccharides and polysaccharides of hyaluronic acid (at least hyaluronic acid hexasaccharide and hyaluronic acid (molecular weight 20,000)) as acceptors.

On the other hand, incorporation of the radioactivity was not found in dermatan sulfate (molecular weight 15,000) and heparin (molecular weight 10,000), showing that they do not substantially function as acceptor substrates.

(6) Analysis of Influence by Temperature

Figure 6:
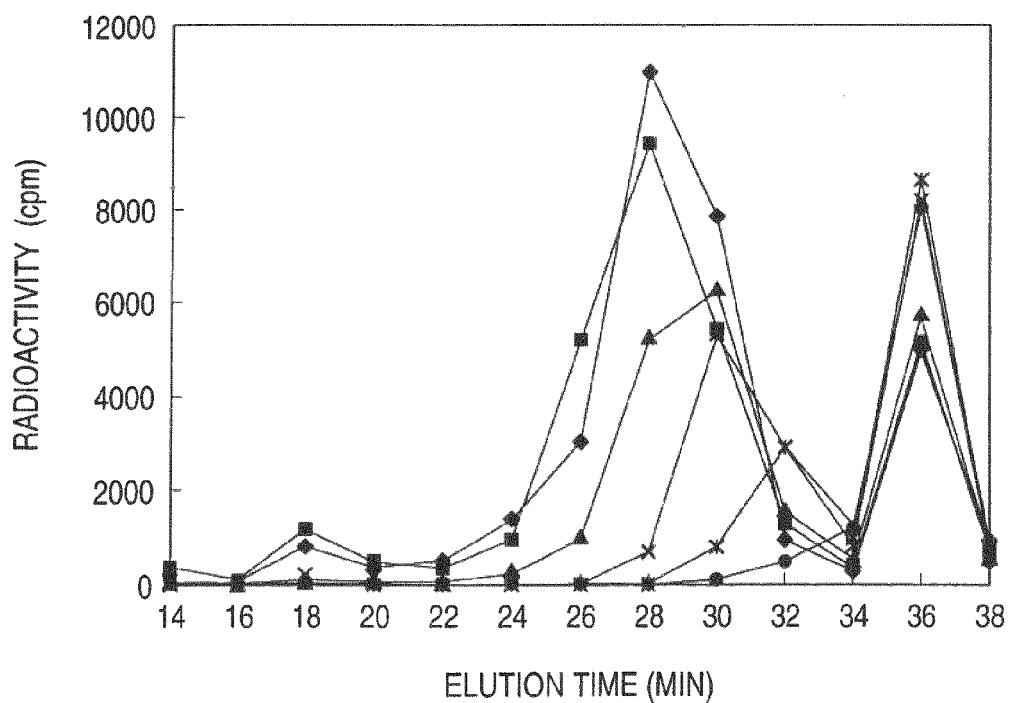
FIG. 6 is a graph showing the influence of temperature on the activity of the enzyme of the present invention.

The enzyme reaction was carried out in the same manner as the above "(2) Analysis of enzyme activity" by changing the enzyme reaction temperature to 25, 30, 37, 40, 45 or 100° C., and the solution after the reaction was applied to a Superdex 75 column (300×φ10 mm: Amersham Biosciences, chromatography conditions; buffer: 0.2 M NaCl, flow rate: 0.5 ml/min). The eluate was fractionated in 1 ml portions and the radioactivity (count of [³H]) of each fraction was measured using a scintillation counter. The results are shown in FIG. 6. Also, the lozenge, square, triangle, x and * marks in FIG. 6 show the results of 25, 30, 37, 40, 45 and 100° C., respectively. Also, the circle in FIG. 6 shows the result of a control (wherein heat-inactivated enzyme of the present invention was used).

As shown in FIG. 6, under the reaction conditions and within the temperature range examined this time, the molecular weight of the reaction product became small as the temperature was increased. The highest incorporation was found at 30° C., but the product having the largest molecular weight was obtained at, 25° C.

It is considered from the results that enzyme activity of the above enzyme of the present invention decreases as the reaction temperature increases starting at 25° C. under the reaction conditions of this time.

(7) Analysis of Influence by Metal Ions and the Like

The enzyme reaction was carried out in the same manner as the above "(2) Analysis of enzyme activity", except that each of various metal salts ($MnCl_2$, $FeCl_2$, $MgCl_2$, $CaCl_2$ or $CuCl_2$) or EDTA was added instead of $MnCl_2$, and the solution after the reaction was applied to a Superdex 75 column (300×φ10 mm: Amersham Biosciences, chromatography conditions; buffer: 0.2 M NaCl, flow rate: 0.5 ml/min). The eluate was fractionated at 1 ml and the radioactivity (count of [³H]) of each fraction was measured using a scintillation counter. Relative values when the radioactivity in addition of $MnCl_2$ was defined as 100% are shown below.

TABLE 3

| Metal salt | Relative value of radioactivity (%) |
|---|---|
| $MnCl_2$ | 100.0 |
| $FeCl_2$ | 30.6 |
| $MgCl_2$ | 30.7 |
| $CaCl_2$ | 0.0 |
| $CuCl_2$ | 0.0 |
| EDTA | 0.0 |

Based on the results; the above enzyme of the present invention showed the highest activity in the presence of $Mn^{2+}$ ion. Also, in the presence of $Fe^{2+}$ or $Mg^{2+}$ ion, it showed about 30% of the activity in comparison with the case of the presence of $Mn^{2+}$ ion. Also, it was shown that it does not substantially act in the presence of $Ca^{2+}$ or $Cu^{2+}$ ion or ethylenediaminetetraacetic acid.

In addition, it was shown that the above enzyme of the present invention acts in the presence of $Fe^{2+}$ or $Mg^{2+}$ ion too, and its enzyme activity in the presence of $Mn^{2+}$ ion is higher than the enzyme activity in the presence of $Fe^{2+}$ or $Mg^{2+}$ ion.

(8) Optimum Reaction pH

When optimum reaction pH of the enzyme of the present invention was examined by changing the pH of the above "(2) Analysis of enzyme activity" to various levels, it was from pH 7.0 to 7.5.

(9) Relation with Enzyme Reaction Time

Figure 7:
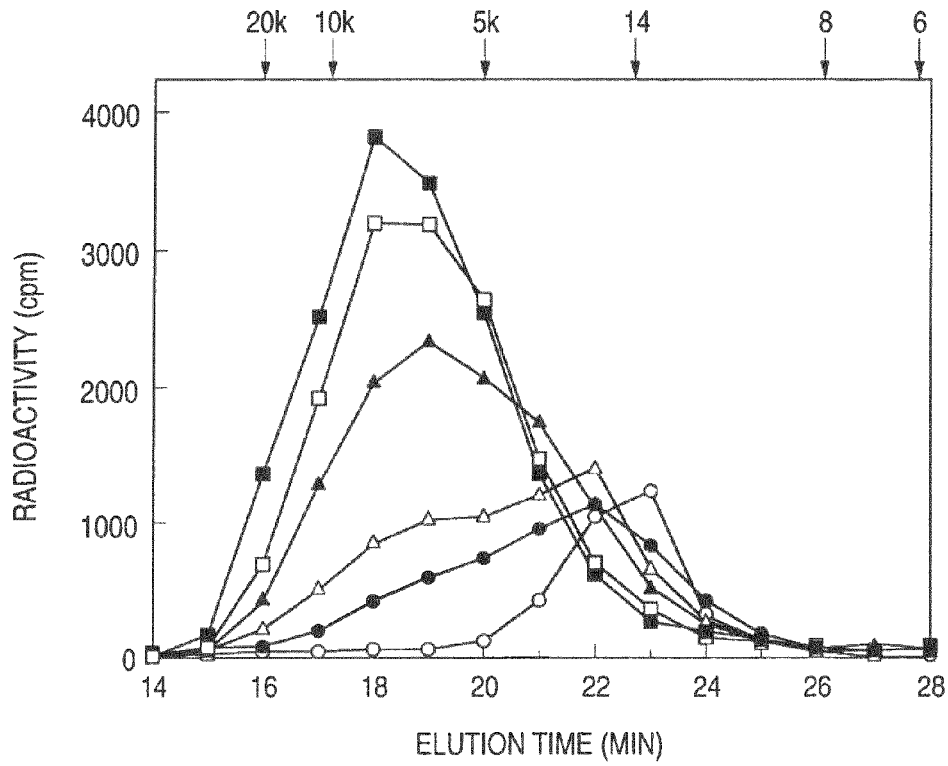
FIG. 7 is a graph showing gel filtration patterns of enzyme reaction products after various enzyme reaction times.

By setting the enzyme reaction time to 10 minutes, 30 minutes, 1 hour, 3 hours, 6 hours or 18 hours, the enzyme reaction was carried out in the same manner as the above "(2) Analysis of enzyme activity", and the radioactivity incorporated into the enzyme reaction product was analyzed. Gel filtration patterns of [³H]GalNAc after various reaction periods are shown in FIG. 7, and the total amounts of the incorporation of radioactivity after various enzyme reaction periods in FIG. 8. The open circle, closed circle, open triangle, closed triangle, open square and closed square show the results after 10 minutes, 30 minutes, 1 hour, 3 hours, 6 hours and 18 hours, respectively. Also, the arrow with "20 k", "10 k", "5 k", "14", "8" or "6" shows the elution position of molecular weight 20,000, 10,000, 5,000, tetradecasaccharide (molecular weight: about 2,800), octasaccharide (molecular weight: about 1,600) or hexasaccharide (molecular weight: about 1,200) of hyaluronic acid (standard), respectively.

Figure 8:
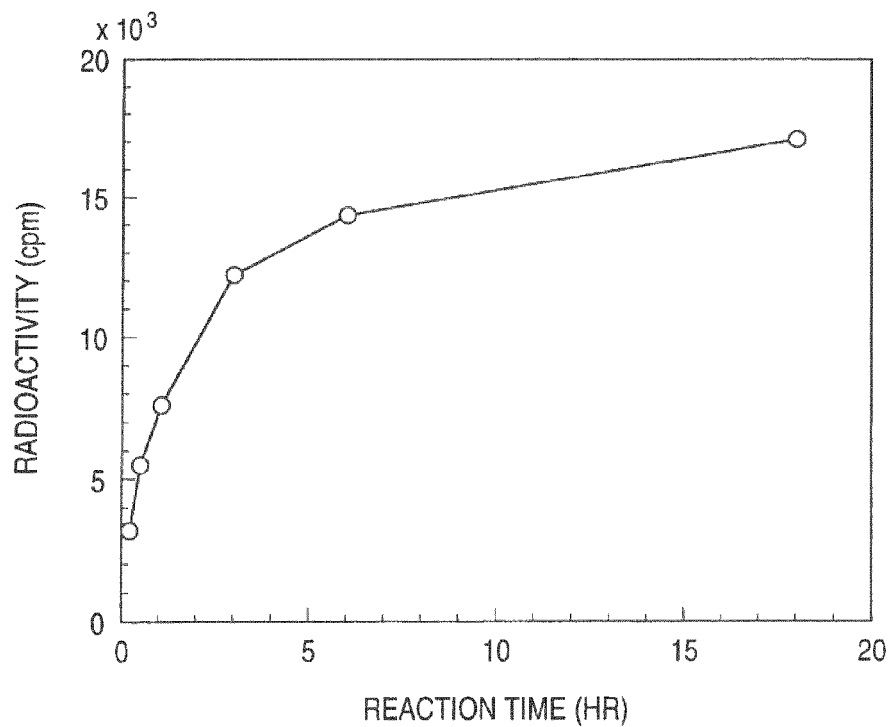
FIG. 8 is a graph showing the relationship between the enzyme reaction time and the incorporation amount of radioactivity.

It was shown from the results of FIG. 8 that under the test conditions, quick incorporation of [³H]GalNAc is found after 3 hours and 6 hours, but the incorporation becomes slow as the reaction draws close to 20 hours.

Also, from the results of FIG. 7, it was shown that the incorporation increases and a reaction product of high molecular weight is obtained after a long period of reaction time.

In addition, a high molecular weight product was quickly obtained when an acceptor substrate (hexasaccharide) was set to a lower concentration, and a low molecular weight product was obtained when the acceptor substrate (hexasaccharide) was set to a high concentration.

(10) Determination of Michaelis Constant (Km)

The radioactivity incorporated into the enzyme reaction product was measured in accordance with the above "(2) Analysis of enzyme activity", by setting using amount of the enzyme of the present invention to 1.3 µg, containing the one donor substrate (UDP-sugar; UDP-GlcUA or UDP-GalNAc) in a fixed concentration (240 µM), and adding thereto the other radio-labeled donor substrate (radiation UDP-sugar; UDP-[$^3$H]GalNAc or UDP-[$^{14}$C]GlcUA) having various (0.6 to 200 µM). Independent tests were carried out three times, and the average value was used as the measured value.

Figure 9:
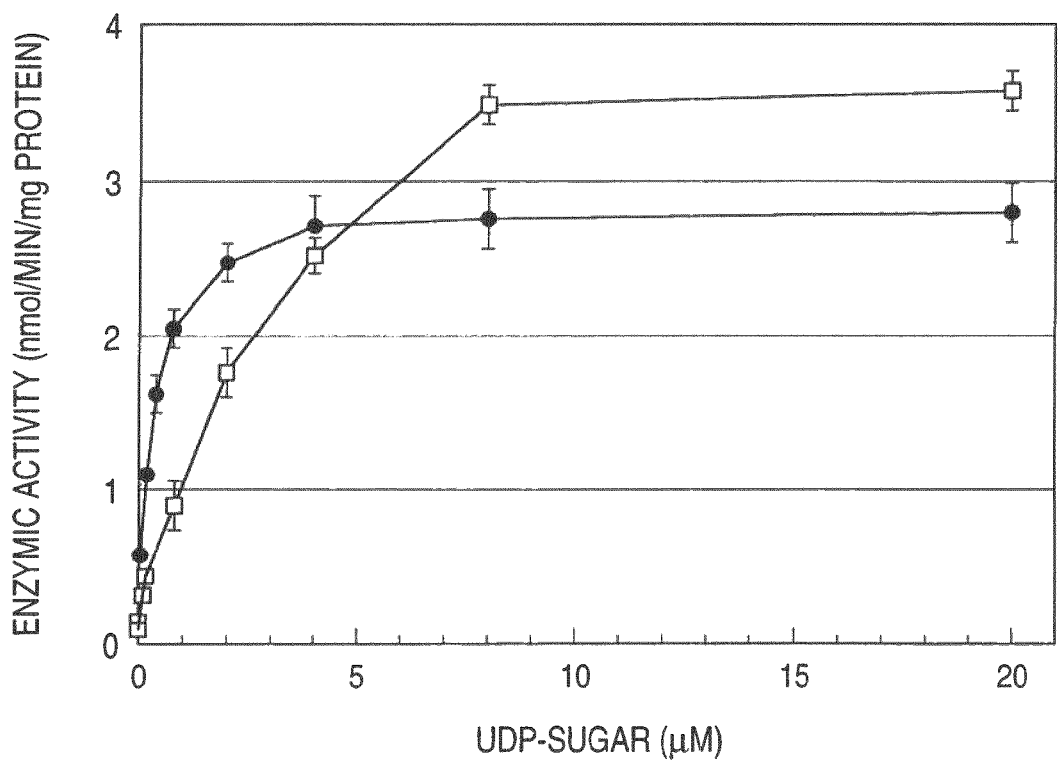
FIG. 9 is a graph showing the relationship between the incorporated radioactivity (V) and the substrate concentration of UDP-sugar (S).
Figure 10:
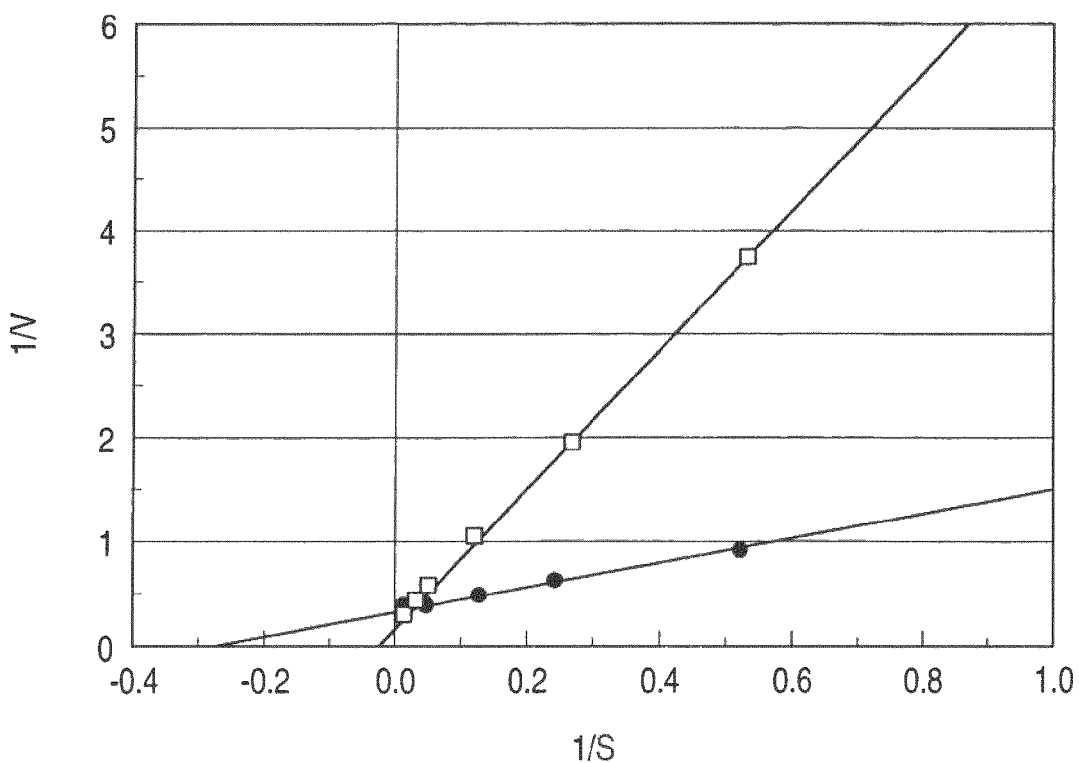
FIG. 10 is a graph showing double reciprocal plots.

Relationship between the incorporated radioactivity (V) and substrate concentration (S) of UDP-sugar is shown in FIG. 9, and its double reciprocal plot in FIG. 10. Closed circle and open square in the drawings show results on UDP-GlcUA and UDP-GalNAc, respectively.

As the result, the Km for UDP-GlcUA and the Km for UDP-GalNAc were calculated to be 3.44 µM and 31.6 µM, respectively.

While the present invention has been described in detail and with reference to specific embodiments thereof, it will be apparent to one of skill in the art that various changes and modifications can be made therein without departing from the spirit and scope thereof. All references cited herein are incorporated in their entirety.

This application is based on Japanese application Nos. 2001-244685, 2001-324127 and 2002-103136 filed on Aug. 10, 2001, Oct. 22, 2001 and Apr. 5, 2002, the entire contents of which are incorporated hereinto by reference.

What is claimed is:

1. A method for producing a sugar chain comprising:
contacting an acceptor sugar chain with at least one GalNAc donor, GlcNAc donor, or GlcUA donor and an isolated protein that has chondroitin polymerase activity;
wherein said isolated protein that has chondroitin polymerase activity comprises SEQ ID NO: 2, or an amino acid sequence identical to SEQ ID NO: 2 except that it has 1 to 30 of its amino acid residue(s) deleted, or substituted, or 1 to 30 amino acid residues inserted within the sequence of SEQ ID NO: 2; wherein said isolated protein is not membrane-bound.

2. The method of claim 1 that produces a sugar chain represented by the formula (3):

GalNAc-GlcUA-X—R¹ (3);

comprising:
contacting the protein that has chondroitin polymerase activity with a GalNAc donor and an acceptor sugar chain represented by the formula (1):

GlcUA-X—R¹ (1);

wherein GlcUA represents D-glucuronic acid; GalNAc represents N-acetyl-D-galactosamine; X represents GalNAc or GlcNAc in which GlcNAc represents N-acetyl-D-glucosamine; - represents a glycosidic linkage; and R¹ represents an any group.

3. The method of claim 1 that produces a sugar chain represented by formula (4):

GlcNAc-GlcUA-X—R¹ (4);

comprising:
contacting the isolated protein having chondroitin polymerase activity with a GlcNAc donor and an acceptor sugar chain represented by the formula (1):

GlcUA-X—R¹ (1);

wherein GlcUA represents D-glucuronic acid; GlcNAc represents N-acetyl-D-glucosamine; X represents GalNAc or GlcNAc in which GalNAc represents N-acetyl-D-galactosamine; - represents a glycosidic linkage; and R¹ represents an any group.

4. The method of claim 1 that produces a sugar chain represented by formula (5):

GlcUA-GalNAc-GlcUA-R² (5);

comprising:
contacting the isolated protein having chondroitin polymerase activity with a GlcUA donor and an acceptor sugar chain represented by the formula (2):

GalNAc-GlcUA-R² (2)

wherein GlcUA represents D-glucuronic acid; GalNAc represents N-acetyl-D-galactosamine; - represents a glycosidic linkage; and R² represents an any group.

5. The method of claim 1 that produces a sugar chain selected from the group consisting of:

(GlcUA-GalNAc)n-GlcUA-X—R¹ (6) and

GalNAc-(GlcUA-GalNAc)n-GlcUA-X—R¹ (8);

comprising:
contacting the isolated protein having chondroitin polymerase activity with a GalNAc donor, a GlcUA donor and an acceptor sugar chain represented by formula (1):

GlcUA-X—R¹ (1);

wherein GlcUA represents D-glucuronic acid; GalNAc represents N-acetyl-D-galactosamine; X represents GalNAc or GlcNAc in which GlcNAc represents N-acetyl-D-glucosamine; - represents a glycosidic linkage; R¹ represents an any group; and n is an integer of 1 or more.

6. The method of claim 1 that produces a sugar chain selected from the group consisting of:

(GalNAc-GlcUA)n-GalNAc-GlcUA-R² (7) and

GlcUA-(GalNAc-GlcUA)n-GalNAc-GlcUA-R² (9);

comprising:
contacting the isolated protein having chondroitin polymerase activity with a GalNAc donor, a GlcUA donor and an acceptor sugar chain represented by formula (2):

GalNAc-GlcUA-R² (2);

wherein GlcUA represents D-glucuronic acid; GalNAc represents N-acetyl-D-galactosamine; - represents a glycosidic linkage; R² represents an any group; and n represents an integer of 1 or more.

7. The method of claim 1, wherein said isolated protein comprises SEQ ID NO: 2 and has chondroitin polymerase activity.

8. The method of claim 1, wherein said isolated protein comprises a sequence identical to SEQ ID NO: 2 except that it has 1 to 30 of its amino acid residue(s) deleted, substituted, or 1 to 30 amino acid residues inserted within the sequence of SEQ ID NO: 2; and wherein said isolated protein has chondroitin polymerase activity.

9. The method of claim 1, wherein said contacting occurs in the presence of at least one of $Mn^{2+}$, $Fe^{2+}$, or $Mg^{2+}$.

10. The method of claim 1, comprising contacting said acceptor sugar chain with nucleoside diphosphate-GlcUA and/or UDP-GlcUA.

11. The method of claim 1, comprising contacting said acceptor sugar chain with a nucleoside diphosphate-GalNAc and/or UDP-GalNAc.

12. The method of claim 1, wherein said acceptor sugar chain has a chondroitin backbone.

13. The method of claim 1, wherein said acceptor sugar chain is an oligosaccharide.

14. The method of claim 1, comprising contacting an acceptor sugar chain that has a hyaluronic acid backbone (a disaccharide repeating structure of GlcUA residue and GlcNAc residue) with a GalNAc donor.

* * * * *

SEQUENCE LISTING

```
<160> NUMBER OF SEQ ID NOS: 12

<210> SEQ ID NO 1
<211> LENGTH: 2058
<212> TYPE: DNA
<213> ORGANISM: Escherichia coli
<220> FEATURE:
<221> NAME/KEY: CDS
<222> LOCATION: (1)..(2058)
<223> OTHER INFORMATION:

<400> SEQUENCE: 1 atg agt att ctt aat caa gca ata aat tta tat aaa aac aaa aat tat        48
Met Ser Ile Leu Asn Gln Ala Ile Asn Leu Tyr Lys Asn Lys Asn Tyr
1               5                   10                  15 cgc caa gct tta tct ctt ttt gag aag gtt gct gaa att tat gat gtt        96
Arg Gln Ala Leu Ser Leu Phe Glu Lys Val Ala Glu Ile Tyr Asp Val
            20                  25                  30 agt tgg gtc gaa gca aat ata aaa tta tgc caa acc gca ctc aat ctt       144
Ser Trp Val Glu Ala Asn Ile Lys Leu Cys Gln Thr Ala Leu Asn Leu
        35                  40                  45 tct gaa gaa gtt gat aag tta aat cgt aaa gct gtt att gat att gat       192
Ser Glu Glu Val Asp Lys Leu Asn Arg Lys Ala Val Ile Asp Ile Asp
    50                  55                  60 gca gca aca aaa ata atg tgt tct aac gcc aaa gca att agt ctg aac       240
Ala Ala Thr Lys Ile Met Cys Ser Asn Ala Lys Ala Ile Ser Leu Asn
65                  70                  75                  80 gag gtt gaa aaa aat gaa ata ata agc aaa tac cga gaa ata acc gca       288
Glu Val Glu Lys Asn Glu Ile Ile Ser Lys Tyr Arg Glu Ile Thr Ala
                85                  90                  95 aag aaa tca gaa cgg gcg gag tta aag gaa gtc gaa ccc att cct tta       336
Lys Lys Ser Glu Arg Ala Glu Leu Lys Glu Val Glu Pro Ile Pro Leu
            100                 105                 110 gat tgg cct agt gat tta act tta ccg ccg tta cct gag agc aca aac       384
Asp Trp Pro Ser Asp Leu Thr Leu Pro Pro Leu Pro Glu Ser Thr Asn
        115                 120                 125 gat tat gtt tgg gcg ggg aaa aga aaa gag ctt gat gat tat cca aga       432
Asp Tyr Val Trp Ala Gly Lys Arg Lys Glu Leu Asp Asp Tyr Pro Arg
    130                 135                 140 aaa cag tta atc att gac ggg ctt agt att gta att cct aca tat aat       480
Lys Gln Leu Ile Ile Asp Gly Leu Ser Ile Val Ile Pro Thr Tyr Asn
145                 150                 155                 160 cga gca aaa ata ctt gca att aca ctt gct tgt ctt tgt aac caa aag       528
Arg Ala Lys Ile Leu Ala Ile Thr Leu Ala Cys Leu Cys Asn Gln Lys
                165                 170                 175
```

```
acc ata tac gac tat gaa gtt att gtt gcc gat gat gga agt aaa gaa      576
Thr Ile Tyr Asp Tyr Glu Val Ile Val Ala Asp Asp Gly Ser Lys Glu
        180                 185                 190 aat att gaa gaa ata gta aga gaa ttt gaa agt tta tta aat ata aaa      624
Asn Ile Glu Glu Ile Val Arg Glu Phe Glu Ser Leu Leu Asn Ile Lys
            195                 200                 205 tat gta cgt cag aag gat tat gga tat caa ctg tgt gct gtt aga aat      672
Tyr Val Arg Gln Lys Asp Tyr Gly Tyr Gln Leu Cys Ala Val Arg Asn
210                 215                 220 ctt ggg ctt agg gct gca aag tat aat tat gtt gca att ctg gat tgt      720
Leu Gly Leu Arg Ala Ala Lys Tyr Asn Tyr Val Ala Ile Leu Asp Cys
225                 230                 235                 240 gat atg gct ccg aac cca cta tgg gtt cag tca tat atg gaa cta tta      768
Asp Met Ala Pro Asn Pro Leu Trp Val Gln Ser Tyr Met Glu Leu Leu
                245                 250                 255 gcg gtg gac gat aat gtt gct cta att ggc cct aga aaa tat ata gat      816
Ala Val Asp Asp Asn Val Ala Leu Ile Gly Pro Arg Lys Tyr Ile Asp
            260                 265                 270 aca agc aag cat aca tat tta gat ttc ctt tcc caa aaa tca cta ata      864
Thr Ser Lys His Thr Tyr Leu Asp Phe Leu Ser Gln Lys Ser Leu Ile
        275                 280                 285 aat gaa att cct gaa atc att act aat aat cag gtt gca ggc aag gtt      912
Asn Glu Ile Pro Glu Ile Ile Thr Asn Asn Gln Val Ala Gly Lys Val
    290                 295                 300 gag caa aac aaa tca gtt gac tgg cga ata gaa cat ttc aaa aat acc      960
Glu Gln Asn Lys Ser Val Asp Trp Arg Ile Glu His Phe Lys Asn Thr
305                 310                 315                 320 gat aat cta aga tta tgc aac aca cca ttt cga ttt ttt agc gga ggt     1008
Asp Asn Leu Arg Leu Cys Asn Thr Pro Phe Arg Phe Phe Ser Gly Gly
                325                 330                 335 aat gtc gct ttt gcg aaa aaa tgg ctt ttc cgt gca gga tgg ttt gat     1056
Asn Val Ala Phe Ala Lys Lys Trp Leu Phe Arg Ala Gly Trp Phe Asp
            340                 345                 350 gaa gag ttt acg cat tgg ggg ggg gag gat aat gag ttt gga tat cgt     1104
Glu Glu Phe Thr His Trp Gly Gly Glu Asp Asn Glu Phe Gly Tyr Arg
        355                 360                 365 ctc tac aga gaa gga tgt tac ttt cgg tct gtt gaa gga gca atg gca     1152
Leu Tyr Arg Glu Gly Cys Tyr Phe Arg Ser Val Glu Gly Ala Met Ala
    370                 375                 380 tat cat caa gaa cca ccc ggg aaa gaa aac gag acg gat cgt gcg gca     1200
Tyr His Gln Glu Pro Pro Gly Lys Glu Asn Glu Thr Asp Arg Ala Ala
385                 390                 395                 400 ggg aaa aat att act gtt caa ttg tta cag caa aaa gtt cct tat ttc     1248
Gly Lys Asn Ile Thr Val Gln Leu Leu Gln Gln Lys Val Pro Tyr Phe
                405                 410                 415 tat aga aaa aaa gaa aaa ata gaa tcc gcg aca tta aaa aga gta cca     1296
Tyr Arg Lys Lys Glu Lys Ile Glu Ser Ala Thr Leu Lys Arg Val Pro
            420                 425                 430 cta gta tct ata tat att ccc gcc tat aac tgc tct aaa tat att gtt     1344
Leu Val Ser Ile Tyr Ile Pro Ala Tyr Asn Cys Ser Lys Tyr Ile Val
        435                 440                 445 cgt tgt gtt gaa agc gcc ctt aat cag aca ata act gac tta gaa gta     1392
Arg Cys Val Glu Ser Ala Leu Asn Gln Thr Ile Thr Asp Leu Glu Val
    450                 455                 460 tgc ata tgc gat gat ggt tcc aca gat gat aca ttg cgg att ctt cag     1440
Cys Ile Cys Asp Asp Gly Ser Thr Asp Asp Thr Leu Arg Ile Leu Gln
465                 470                 475                 480 gag cat tat gca aac cat cct cga gtt cgt ttt att tca caa aaa aac     1488
Glu His Tyr Ala Asn His Pro Arg Val Arg Phe Ile Ser Gln Lys Asn
                485                 490                 495
```

```
aaa gga att ggt tca gca tct aat aca gca gtt aga ttg tgt cgg gga    1536
Lys Gly Ile Gly Ser Ala Ser Asn Thr Ala Val Arg Leu Cys Arg Gly
            500                 505                 510 ttc tat ata ggt cag tta gac tct gat gac ttt ctt gaa cca gat gct    1584
Phe Tyr Ile Gly Gln Leu Asp Ser Asp Asp Phe Leu Glu Pro Asp Ala
        515                 520                 525 gtt gaa cta tgt cta gat gaa ttt aga aaa gat cta tca ttg gca tgt    1632
Val Glu Leu Cys Leu Asp Glu Phe Arg Lys Asp Leu Ser Leu Ala Cys
    530                 535                 540 gtt tat aca act aac cgt aat ata gat cgt gaa ggt aat ttg ata tca    1680
Val Tyr Thr Thr Asn Arg Asn Ile Asp Arg Glu Gly Asn Leu Ile Ser
545                 550                 555                 560 aat ggc tat aat tgg ccc att tat tcg cga gaa aaa ctt act agt gca    1728
Asn Gly Tyr Asn Trp Pro Ile Tyr Ser Arg Glu Lys Leu Thr Ser Ala
                565                 570                 575 atg ata tgt cat cat ttc agg atg ttc aca gca aga gca tgg aac cta    1776
Met Ile Cys His His Phe Arg Met Phe Thr Ala Arg Ala Trp Asn Leu
            580                 585                 590 act gaa ggt ttc aac gaa tcg atc agc aac gca gtt gat tac gat atg    1824
Thr Glu Gly Phe Asn Glu Ser Ile Ser Asn Ala Val Asp Tyr Asp Met
        595                 600                 605 tat tta aaa ctt agt gaa gtt gga ccg ttc aag cat ata aac aaa att    1872
Tyr Leu Lys Leu Ser Glu Val Gly Pro Phe Lys His Ile Asn Lys Ile
    610                 615                 620 tgt tat aat cgc gta ttg cat ggt gaa aat acg tct ata aaa aag ttg    1920
Cys Tyr Asn Arg Val Leu His Gly Glu Asn Thr Ser Ile Lys Lys Leu
625                 630                 635                 640 gat att caa aag gaa aat cat ttt aaa gtt gtt aac gaa tca tta agt    1968
Asp Ile Gln Lys Glu Asn His Phe Lys Val Val Asn Glu Ser Leu Ser
                645                 650                 655 agg cta ggc ata aaa aaa tat aaa tat tca cca tta act aat ttg aat    2016
Arg Leu Gly Ile Lys Lys Tyr Lys Tyr Ser Pro Leu Thr Asn Leu Asn
            660                 665                 670 gaa tgt aga aaa tat acc tgg gaa aaa ata gag aat gat tta            2058
Glu Cys Arg Lys Tyr Thr Trp Glu Lys Ile Glu Asn Asp Leu
        675                 680                 685

<210> SEQ ID NO 2
<211> LENGTH: 686
<212> TYPE: PRT
<213> ORGANISM: Escherichia coli

<400> SEQUENCE: 2

Met Ser Ile Leu Asn Gln Ala Ile Asn Leu Tyr Lys Asn Lys Asn Tyr
1               5                   10                  15

Arg Gln Ala Leu Ser Leu Phe Glu Lys Val Ala Glu Ile Tyr Asp Val
            20                  25                  30

Ser Trp Val Glu Ala Asn Ile Lys Leu Cys Gln Thr Ala Leu Asn Leu
        35                  40                  45

Ser Glu Glu Val Asp Lys Leu Asn Arg Lys Ala Val Ile Asp Ile Asp
    50                  55                  60

Ala Ala Thr Lys Ile Met Cys Ser Asn Ala Lys Ala Ile Ser Leu Asn
65                  70                  75                  80

Glu Val Glu Lys Asn Glu Ile Ile Ser Lys Tyr Arg Glu Ile Thr Ala
                85                  90                  95

Lys Lys Ser Glu Arg Ala Glu Leu Lys Glu Val Glu Pro Ile Pro Leu
            100                 105                 110

Asp Trp Pro Ser Asp Leu Thr Leu Pro Pro Leu Pro Glu Ser Thr Asn
        115                 120                 125
```

-continued

```
Asp Tyr Val Trp Ala Gly Lys Arg Lys Glu Leu Asp Asp Tyr Pro Arg
        130                 135                 140

Lys Gln Leu Ile Ile Asp Gly Leu Ser Ile Val Ile Pro Thr Tyr Asn
145                 150                 155                 160

Arg Ala Lys Ile Leu Ala Ile Thr Leu Ala Cys Leu Cys Asn Gln Lys
                165                 170                 175

Thr Ile Tyr Asp Tyr Glu Val Ile Val Ala Asp Asp Gly Ser Lys Glu
            180                 185                 190

Asn Ile Glu Glu Ile Val Arg Glu Phe Glu Ser Leu Leu Asn Ile Lys
        195                 200                 205

Tyr Val Arg Gln Lys Asp Tyr Gly Tyr Gln Leu Cys Ala Val Arg Asn
210                 215                 220

Leu Gly Leu Arg Ala Ala Lys Tyr Asn Tyr Val Ala Ile Leu Asp Cys
225                 230                 235                 240

Asp Met Ala Pro Asn Pro Leu Trp Val Gln Ser Tyr Met Glu Leu Leu
                245                 250                 255

Ala Val Asp Asp Asn Val Ala Leu Ile Gly Pro Arg Lys Tyr Ile Asp
            260                 265                 270

Thr Ser Lys His Thr Tyr Leu Asp Phe Leu Ser Gln Lys Ser Leu Ile
        275                 280                 285

Asn Glu Ile Pro Glu Ile Ile Thr Asn Gln Val Ala Gly Lys Val
290                 295                 300

Glu Gln Asn Lys Ser Val Asp Trp Arg Ile Glu His Phe Lys Asn Thr
305                 310                 315                 320

Asp Asn Leu Arg Leu Cys Asn Thr Pro Phe Arg Phe Ser Gly Gly
                325                 330                 335

Asn Val Ala Phe Ala Lys Lys Trp Leu Phe Arg Ala Gly Trp Phe Asp
            340                 345                 350

Glu Glu Phe Thr His Trp Gly Gly Glu Asp Asn Glu Phe Gly Tyr Arg
        355                 360                 365

Leu Tyr Arg Glu Gly Cys Tyr Phe Arg Ser Val Glu Gly Ala Met Ala
370                 375                 380

Tyr His Gln Glu Pro Pro Gly Lys Glu Asn Glu Thr Asp Arg Ala Ala
385                 390                 395                 400

Gly Lys Asn Ile Thr Val Gln Leu Leu Gln Gln Lys Val Pro Tyr Phe
                405                 410                 415

Tyr Arg Lys Lys Glu Lys Ile Glu Ser Ala Thr Leu Lys Arg Val Pro
            420                 425                 430

Leu Val Ser Ile Tyr Ile Pro Ala Tyr Asn Cys Ser Lys Tyr Ile Val
        435                 440                 445

Arg Cys Val Glu Ser Ala Leu Asn Gln Thr Ile Thr Asp Leu Glu Val
450                 455                 460

Cys Ile Cys Asp Asp Gly Ser Thr Asp Thr Leu Arg Ile Leu Gln
465                 470                 475                 480

Glu His Tyr Ala Asn His Pro Arg Val Arg Phe Ile Ser Gln Lys Asn
                485                 490                 495

Lys Gly Ile Gly Ser Ala Ser Asn Thr Ala Val Arg Leu Cys Arg Gly
            500                 505                 510

Phe Tyr Ile Gly Gln Leu Asp Ser Asp Phe Leu Glu Pro Asp Ala
        515                 520                 525

Val Glu Leu Cys Leu Asp Glu Phe Arg Lys Asp Leu Ser Leu Ala Cys
530                 535                 540

Val Tyr Thr Thr Asn Arg Asn Ile Asp Arg Glu Gly Asn Leu Ile Ser
```

```
               545                 550                 555                 560
Asn Gly Tyr Asn Trp Pro Ile Tyr Ser Arg Glu Lys Leu Thr Ser Ala
                565                 570                 575

Met Ile Cys His His Phe Arg Met Phe Thr Ala Arg Ala Trp Asn Leu
            580                 585                 590

Thr Glu Gly Phe Asn Glu Ser Ile Ser Asn Ala Val Asp Tyr Asp Met
        595                 600                 605

Tyr Leu Lys Leu Ser Glu Val Gly Pro Phe Lys His Ile Asn Lys Ile
    610                 615                 620

Cys Tyr Asn Arg Val Leu His Gly Glu Asn Thr Ser Ile Lys Lys Leu
625                 630                 635                 640

Asp Ile Gln Lys Glu Asn His Phe Lys Val Val Asn Glu Ser Leu Ser
                645                 650                 655

Arg Leu Gly Ile Lys Lys Tyr Lys Tyr Ser Pro Leu Thr Asn Leu Asn
            660                 665                 670

Glu Cys Arg Lys Tyr Thr Trp Glu Lys Ile Glu Asn Asp Leu
        675                 680                 685

<210> SEQ ID NO 3
<211> LENGTH: 14483
<212> TYPE: DNA
<213> ORGANISM: Escherichia coli
<220> FEATURE:
<221> NAME/KEY: CDS
<222> LOCATION: (3787)..(5847)
<223> OTHER INFORMATION:

<400> SEQUENCE: 3
cgacattatg tctttaagaa tttaaatatt gaaatcccct caggaaaaag tgttgccttt      60
attggtcgta atggtgcggg taaatcaacg ttactgagaa tgattggtgg cattgaccgc    120
cccgatagcg gaaagatcat caccaataaa acgatatcat ggccagtcgg ccttgcaggt    180
ggatttcagg gaagtttaac cggacgcgaa aatgtaaaat ttgtcgcgag gttatacgcg    240
aagcaagaag aactgaaaga gaaaattgag tttgttgaag aatttgccga actcggcaag    300
tattttgata tgccgatcaa aacttactcc tctggtatgc gatctcgcct aggctttggt    360
ttaagtatgg catttaaatt tgattattat atcgtcgatg aagtaaccgc agtcggtgat    420
gccaggttta agaaaaatg cgctcaattg tttaagaaa ggcataaaga atctagtttt    480
ttaatggttt cacatagttt gaattcattg aaagagtttt gtgatgtggc cattgttttt    540
aaggatgaca atgcggttag ttttcatgag gatgttcagg agggataga agagtatata    600 acggaacaaa ataattactg atgttgtttt caagggtgaa aaatgaatat attagttaca    660
ggtggagcag gctatattgg ctcgcatact agtttatgtc ttctgaataa aggttacaat    720
gttgtaatca ttgacaactt aattaattca tcttgcgaga gcattcgaag gattgaatta    780
atagctaaaa aaaagttac tttctatgag ttgaacatca acaatgaaaa agaagttaat    840
caaattctaa aaaacacaa atttgattgt ataatgcatt ttgccggtgc aaagtctgtt    900
gctgaatctt taataaaacc cattttttat tatgataata atgtttcagg acgttgcaa    960 ttaattaatt gcgctataaa aaacgatgtg gctaattta tttttagctc ttctgcaacg   1020
gtttatggtg aaagcaaaat aatgcctgta acagaagatt gccatatagg aggaacatta   1080
aatccatatg gtacatcaaa gtatatatca gaattgatga ttagagatat tgcaaaaaaa   1140
tatagcgata ctaattttttt gtgtctgaga tattttaacc caacaggtgc tcacgagtcg   1200
ggaatgatcg gtgaaagtcc cgctgatata ccaagcaatt tagttcctta tatattacaa   1260
```

```
gttgctatgg gtaaactaga aaaacttatg gtgtttgggg gggattaccc tacaaaggat    1320
ggaaccggtg ttcgtgatta tatacacgta atggatttag cggaagggca tgtggctgct    1380
ttatcttacc ttttccgtga taataacact aattatcatg tttttaattt aggtactggt    1440
aaaggatatt ctgttttaga gctggtttct acctttgaaa aaatatctgg ggttagaatt    1500
ccatatgaaa ttgtttcgag aagagatggg gatattgctg aaagttggtc atcaccagaa    1560
aaagcaaata agtatctcaa ttggaaagct aaaaggggat tggaaacaat gcttgaggat    1620
gcctggcgct ggcaaatgaa aaacccaaat ggttatattt aatcatgcat aaggtaaagc    1680
aaaattttac gataacttct atatctattg gcatcttaat aatcgaaatt tagtgtggtg    1740
aattggttta ataaattcgt agacactaaa aagtagatgg ggtgttaatt aaagctaact    1800
aaacaaatgg cgaataaagg gttttctgcc ttgggggat aaaacatcat gaatagacta    1860
gtaatagttg gtcatccgag ctctaattat caaattgtag aagaactttt gcatcaaaga    1920
ggaatgaatt ctctatgtcc atcgaagcga gataatttaa gcccccaaga tatcactcag    1980
acgcttcgta aggcatatca atcccctgat atatacactg taacagatag tgctgatttc    2040
gaaccattac acgtttctac tgtctggaat ggtatagccc ttgacttgat gcttagtaat    2100
ttgaaccaaa aattgtgcgg atggtcggat cctaatgcaa tccatacatt agaatattgg    2160
aagagtgttg atgaaaacat tacatttatt ctaatttacg atcatccaaa gtctatttta    2220
acaaattatt tttcagatca aaatatatcg tccaactata cgtcagaaca tttaattaaa    2280
aactggcttg cctataatac agcattgtta cactttttc ttaataatcg cggtaggtgt    2340
ttattagtaa gctcagaaca agtcaaacgt aatgcagagg attgcataca acaacttcaa    2400
cataagctta agttgaaatt tggtctttca ttttcaaata cgattaatca ttcactagaa    2460
caatctgtaa atgattttaa gacggctgaa gcttcgatta ctctggaaaa agagcatcag    2520
gaaataatgt ctctatcagg tattgatata ggaaccggag atattatatt caaacagagt    2580
gaaacagagg aatatttaat tttcaatgta ttgaatgatt atccagattg taaagagctt    2640 tatttttgaat tacaatctaa tgcaaatact ccgcttaggg ttttagaaaa ggaaaattac    2700
aagccttcct ttatatggga gacatttata aaacaacgcc aaataacatt agatattgtc    2760
aatggattat atcagtcctc taaaaaaata attttagata acgagttaca cacatcaaaa    2820
caattaaatg catatcaggc tatttttaaaa gaattgagtg actctaaaga agaattgatt    2880
caatatgatt taataataaa aaataagaca atacaagttc aggagcttga atgcgccata    2940
gaaaattttg aatcgctgtt aaagaaagaa caaaataaaa atgaattgca acaacaaaga    3000
ttggaaaaat taagttgtga aaagaactac ctgcttaatc aattgcattt agtacaacaa    3060
aaacttgaac aatattttat tgataatcaa cgattagaaa aaaacaact tccagaatta    3120 tatggtgcag cagaacgtat aacacaggac attggatatc gcctgggtgc tgtaatggtt    3180
agtcgttcaa aaacattttt aggattaatt agcattcctt ttgctttgat atccgaatgg    3240
cgaacatgga aaagaaata cgatagtgaa tatcaagtct ctctgccatc aatatttctt    3300
tatgctgata acatgaggc agaaagggtg aaaaaacatt tatcctatca attaggaaaa    3360
ttaatcataa atcaaaatca ttttccacta gggttgatat ctttgccatt ttcgatatac    3420
agaacaatac gtcaattcaa aagaacaaaa ataattctc aggtagggt taaatactgt    3480 ggaaaataaa tccaggctac taaatataaa gttaaaatat cggctataaa tgcgtgcgaa    3540
ttaatagtga aaattttctt agttaagtga aatagctttt ttctaattgt ttaagtcata    3600
gtggtttacg ctttatttaa ttaaaaaaat aaaataataa attaaaata cgattctcaa    3660
```

```
                                                      -continued tatttcttca agtatcaatt aggatttaat ggggcaagat tatgatatcg catgaaaata     3720
tatatatagg gacatgatta ttatgcgtgt tgatacttta attatactag attaggttga     3780 aataat atg agt att ctt aat caa gca ata aat tta tat aaa aac aaa       3828
       Met Ser Ile Leu Asn Gln Ala Ile Asn Leu Tyr Lys Asn Lys
        1               5                   10 aat tat cgc caa gct tta tct ctt ttt gag aag gtt gct gaa att tat     3876
Asn Tyr Arg Gln Ala Leu Ser Leu Phe Glu Lys Val Ala Glu Ile Tyr
 15          20                  25                  30 gat gtt agt tgg gtc gaa gca aat ata aaa tta tgc caa acc gca ctc     3924
Asp Val Ser Trp Val Glu Ala Asn Ile Lys Leu Cys Gln Thr Ala Leu
                 35                  40                  45 aat ctt tct gaa gaa gtt gat aag tta aat cgt aaa gct gtt att gat     3972
Asn Leu Ser Glu Glu Val Asp Lys Leu Asn Arg Lys Ala Val Ile Asp
             50                  55                  60 att gat gca gca aca aaa ata atg tgt tct aac gcc aaa gca att agt     4020
Ile Asp Ala Ala Thr Lys Ile Met Cys Ser Asn Ala Lys Ala Ile Ser
         65                  70                  75 ctg aac gag gtt gaa aaa aat gaa ata ata agc aaa tac cga gaa ata     4068
Leu Asn Glu Val Glu Lys Asn Glu Ile Ile Ser Lys Tyr Arg Glu Ile
 80                  85                  90 acc gca aag aaa tca gaa cgg gcg gag tta aag gaa gtc gaa ccc att     4116
Thr Ala Lys Lys Ser Glu Arg Ala Glu Leu Lys Glu Val Glu Pro Ile
 95                 100                 105                 110 cct tta gat tgg cct agt gat tta act tta ccg ccg tta cct gag agc     4164
Pro Leu Asp Trp Pro Ser Asp Leu Thr Leu Pro Pro Leu Pro Glu Ser
                115                 120                 125 aca aac gat tat gtt tgg gcg ggg aaa aga aaa gag ctt gat gat tat     4212
Thr Asn Asp Tyr Val Trp Ala Gly Lys Arg Lys Glu Leu Asp Asp Tyr
            130                 135                 140 cca aga aaa cag tta atc att gac ggg ctt agt att gta att cct aca     4260
Pro Arg Lys Gln Leu Ile Ile Asp Gly Leu Ser Ile Val Ile Pro Thr
        145                 150                 155 tat aat cga gca aaa ata ctt gca att aca ctt gct tgt ctt tgt aac     4308
Tyr Asn Arg Ala Lys Ile Leu Ala Ile Thr Leu Ala Cys Leu Cys Asn
160                 165                 170 caa aag acc ata tac gac tat gaa gtt att gtt gcc gat gat gga agt     4356
Gln Lys Thr Ile Tyr Asp Tyr Glu Val Ile Val Ala Asp Asp Gly Ser
175                 180                 185                 190 aaa gaa aat att gaa gaa ata gta aga gaa ttt gaa agt tta tta aat     4404
Lys Glu Asn Ile Glu Glu Ile Val Arg Glu Phe Glu Ser Leu Leu Asn
                195                 200                 205 ata aaa tat gta cgt cag aag gat tat gga tat caa ctg tgt gct gtt     4452
Ile Lys Tyr Val Arg Gln Lys Asp Tyr Gly Tyr Gln Leu Cys Ala Val
            210                 215                 220 aga aat ctt ggg ctt agg gct gca aag tat aat tat gtt gca att ctg     4500
Arg Asn Leu Gly Leu Arg Ala Ala Lys Tyr Asn Tyr Val Ala Ile Leu
        225                 230                 235 gat tgt gat atg gct ccg aac cca cta tgg gtt cag tca tat atg gaa     4548
Asp Cys Asp Met Ala Pro Asn Pro Leu Trp Val Gln Ser Tyr Met Glu
    240                 245                 250 cta tta gcg gtg gac gat aat gtt gct cta att ggc cct aga aaa tat     4596
Leu Leu Ala Val Asp Asp Asn Val Ala Leu Ile Gly Pro Arg Lys Tyr
255                 260                 265                 270 ata gat aca agc aag cat aca tat tta gat ttc ctt tcc caa aaa tca     4644
Ile Asp Thr Ser Lys His Thr Tyr Leu Asp Phe Leu Ser Gln Lys Ser
                275                 280                 285 cta ata aat gaa att cct gaa atc att act aat aat cag gtt gca ggc     4692
Leu Ile Asn Glu Ile Pro Glu Ile Ile Thr Asn Asn Gln Val Ala Gly
            290                 295                 300
```

```
aag gtt gag caa aac aaa tca gtt gac tgg cga ata gaa cat ttc aaa    4740
Lys Val Glu Gln Asn Lys Ser Val Asp Trp Arg Ile Glu His Phe Lys
            305                 310                 315 aat acc gat aat cta aga tta tgc aac aca cca ttt cga ttt ttt agc    4788
Asn Thr Asp Asn Leu Arg Leu Cys Asn Thr Pro Phe Arg Phe Phe Ser
        320                 325                 330 gga ggt aat gtc gct ttt gcg aaa aaa tgg ctt ttc cgt gca gga tgg    4836
Gly Gly Asn Val Ala Phe Ala Lys Lys Trp Leu Phe Arg Ala Gly Trp
335                 340                 345                 350 ttt gat gaa gag ttt acg cat tgg ggg ggg gag gat aat gag ttt gga    4884
Phe Asp Glu Glu Phe Thr His Trp Gly Gly Glu Asp Asn Glu Phe Gly
                355                 360                 365 tat cgt ctc tac aga gaa gga tgt tac ttt cgg tct gtt gaa gga gca    4932
Tyr Arg Leu Tyr Arg Glu Gly Cys Tyr Phe Arg Ser Val Glu Gly Ala
            370                 375                 380 atg gca tat cat caa gaa cca ccc ggg aaa gaa aac gag acg gat cgt    4980
Met Ala Tyr His Gln Glu Pro Pro Gly Lys Glu Asn Glu Thr Asp Arg
        385                 390                 395 gcg gca ggg aaa aat att act gtt caa ttg tta cag caa aaa gtt cct    5028
Ala Ala Gly Lys Asn Ile Thr Val Gln Leu Leu Gln Gln Lys Val Pro
400                 405                 410 tat ttc tat aga aaa aaa gaa aaa ata gaa tcc gcg aca tta aaa aga    5076
Tyr Phe Tyr Arg Lys Lys Glu Lys Ile Glu Ser Ala Thr Leu Lys Arg
415                 420                 425                 430 gta cca cta gta tct ata tat att ccc gcc tat aac tgc tct aaa tat    5124
Val Pro Leu Val Ser Ile Tyr Ile Pro Ala Tyr Asn Cys Ser Lys Tyr
                435                 440                 445 att gtt cgt tgt gtt gaa agc gcc ctt aat cag aca ata act gac tta    5172
Ile Val Arg Cys Val Glu Ser Ala Leu Asn Gln Thr Ile Thr Asp Leu
            450                 455                 460 gaa gta tgc ata tgc gat gat ggt tcc aca gat gat aca ttg cgg att    5220
Glu Val Cys Ile Cys Asp Asp Gly Ser Thr Asp Asp Thr Leu Arg Ile
        465                 470                 475 ctt cag gag cat tat gca aac cat cct cga gtt cgt ttt att tca caa    5268
Leu Gln Glu His Tyr Ala Asn His Pro Arg Val Arg Phe Ile Ser Gln
    480                 485                 490 aaa aac aaa gga att ggt tca gca tct aat aca gca gtt aga ttg tgt    5316
Lys Asn Lys Gly Ile Gly Ser Ala Ser Asn Thr Ala Val Arg Leu Cys
495                 500                 505                 510 cgg gga ttc tat ata ggt cag tta gac tct gat gac ttt ctt gaa cca    5364
Arg Gly Phe Tyr Ile Gly Gln Leu Asp Ser Asp Asp Phe Leu Glu Pro
                515                 520                 525 gat gct gtt gaa cta tgt cta gat gaa ttt aga aaa gat cta tca ttg    5412
Asp Ala Val Glu Leu Cys Leu Asp Glu Phe Arg Lys Asp Leu Ser Leu
            530                 535                 540 gca tgt gtt tat aca act aac cgt aat ata gat cgt gaa ggt aat ttg    5460
Ala Cys Val Tyr Thr Thr Asn Arg Asn Ile Asp Arg Glu Gly Asn Leu
        545                 550                 555 ata tca aat ggc tat aat tgg ccc att tat tcg cga gaa aaa ctt act    5508
Ile Ser Asn Gly Tyr Asn Trp Pro Ile Tyr Ser Arg Glu Lys Leu Thr
    560                 565                 570 agt gca atg ata tgt cat cat ttc agg atg ttc aca gca aga gca tgg    5556
Ser Ala Met Ile Cys His His Phe Arg Met Phe Thr Ala Arg Ala Trp
575                 580                 585                 590 aac cta act gaa ggt ttc aac gaa tcg atc agc aac gca gtt gat tac    5604
Asn Leu Thr Glu Gly Phe Asn Glu Ser Ile Ser Asn Ala Val Asp Tyr
                595                 600                 605 gat atg tat tta aaa ctt agt gaa gtt gga ccg ttc aag cat ata aac    5652
Asp Met Tyr Leu Lys Leu Ser Glu Val Gly Pro Phe Lys His Ile Asn
            610                 615                 620
```

```
aaa att tgt tat aat cgc gta ttg cat ggt gaa aat acg tct ata aaa        5700
Lys Ile Cys Tyr Asn Arg Val Leu His Gly Glu Asn Thr Ser Ile Lys
            625                 630                 635 aag ttg gat att caa aag gaa aat cat ttt aaa gtt gtt aac gaa tca        5748
Lys Leu Asp Ile Gln Lys Glu Asn His Phe Lys Val Val Asn Glu Ser
        640                 645                 650 tta agt agg cta ggc ata aaa aaa tat aaa tat tca cca tta act aat        5796
Leu Ser Arg Leu Gly Ile Lys Lys Tyr Lys Tyr Ser Pro Leu Thr Asn
655                 660                 665                 670 ttg aat gaa tgt aga aaa tat acc tgg gaa aaa ata gag aat gat tta        5844
Leu Asn Glu Cys Arg Lys Tyr Thr Trp Glu Lys Ile Glu Asn Asp Leu
                675                 680                 685 taa ttattgatat attacaagtg ataaacatgt agactggccc cctgaatctc             5897
cagacaacca atatcactta ataagtgat agtcttaata ctagttttta gactagtcat       5957
tggagaacag atgattgatg tcttagggcc ggagaaacgc agacggcgta ctacacagga      6017
aaagatcgct atcgttcagc agagctttga accgggaatg acgtctccc ttgttgcccg       6077 gcaacatggt gtggcagcca gccagctatt tctctggcgt aagcaatacc aggagggaag      6137
tcttactgct gtggctgccg gagaacaggt cgttcctgcc tctgaacttg ctgccgccat      6197
gaagcagatt aaagaactcc agcgtctgct cggcaaaaaa acgatggaaa atgaactcct      6257
taaagaagcc gttgaatatg ggcgagcaaa aaagtggata gcgcacgcgc ccttattgcc      6317
cggggatggg gagtaagctt cgtcagccgt tgtctccggg tgtcgcgtgc gcagttgcac      6377
gtcattctca gacgagccga tgactggaag gacggccgcc gcagccgtca cacgatgat      6437 acggatgtgc ttcgccgtat acaccatgtt atcggagagc tgcccacgta tggttatcgt     6497
cgggtatggg cgctgcttcg cagacaaaca gaacttgatg gtatgcctgc gatcaatgcc     6557
aaacgtgttt accggaccat cgccagaat gcgctgttgc ttgagcgaaa acccgctgta      6617
ccgccatcga aacgggcaca taccggcaga gtggctgtga agaaagtaa tcagcgatgg      6677 tgctctgacg ggtttgagtt ccgctgtgat aacgagaaa aactgcgggt cacgttcgcg      6737
ctggactgct gtgaccgtga ggcactgcac tgggcggtca caacgggtgg cttcgacagt     6797
gaaacagtac aggacgtcat gctgggagca gtggaacgcc gctttggcag cgagcttccg     6857
gcgtctccag tggagtggct gacggataat ggttcatgct accgggcgaa tgaaacacgt     6917
cagttcgcca ggatgttggg acttgaaccg aagaacacgg cagtgcgag tccgagagt      6977 aacggaatag cagagagctt cgtgaaaacg ataaagcgtg actacataag tatcatgccc     7037
aaaccagacg ggtaacggc agcaaagaac cttgcagagg cgttcgagca ttataacgaa      7097
tggcatccgc atagtgcgct gggttatcgc tcgccacggg aatatctgcg gcagtgggcc     7157
agtgatgggt aagtgataa caggtatctg gaaacatagg ggcaaatcca acatgctaaa      7217
aaacttaaca tttgatcata tattaagtct ttcaaagaaa gaagataaaa ttaaacttgt     7277
acaattaatt gtaaatcatt tagatgagag aacattaagc tgtataaaaa atatctctac     7337
tggtaaggga tttaatgctc atttaaaaat acttgaactt tttgacctat ggttgagtga     7397
gtattttgaa tatattatta tacctaataa gttaagcaat gcagggactt tttattttgc     7457
attctttttt cccgagtttt atattaaaag attcaataag aataatactg atctttcctc     7517
gttaggagac acatctttta aacgactat gagtcgacca catataccaa actatgttta      7577
caatcttgtg ataaactcta atggatgtac ttttaactcc attaaattat tattgctggc     7637
tcttagtcta acatcaaaaa ggttttatga aacacctcag caagaacgta atttttttgtg    7697 tcatataaat gaaattgtct tggctaatgc tgacgaatac tccggtatca tttcttgcat     7757
```

```
tataaaaagt agaatatctg taattgatga ctttatttca agtaatgttt cattaaatac      7817
aaacaggcaa atagctttat tcataactgg acaatcaaga ggttttatag atgccctacc      7877
taatctcgta agtgaaataa cgattccttc tgatgttgat gttttattta gtacatggaa      7937
agatatcgga cacacacagt tatctaaaga aagaatatgt aggatatttg acagcgaggc      7997
tgcacaatat gtttcagagc cagataacta ctcgtttgta gacgaacact atgatgaatt      8057
aaaagacttg agcttaagtt catataaaaa taataattta gaggagatat attcaagttt      8117
tttctctgga tgtaactcag ttttaataaa cattaaagat gatgggaat atccatataa       8177 taaaatgagt aatgcagaaa aaatgtatta ccataattca ttttggttct gtagtcttaa      8237
aaatcataat tgggataaat ataggtgcat tataaagata aggcctgatg ctttattgca      8297
agtggataat gtgacaatta atgatataga tgtagatgat tctgtttatt gtgaggatag      8357
taatgggtgg atatttagag aatggggtt tggcataggc gaccaattat tttacggcga       8417
tcctgatata atgaaaaagc tgatgtgtgt ccatggttta gaaaaaatat atagtcagct      8477
aacatccttg atctcaagtt ctaatgttta ttattcaggt catattaatg tagggttatg      8537
tgcttgggct aatgtatatg attgccaggt ttctaattta aaaataaaaa atattgttag      8597
cgcctcgaaa aatatcgcta gaacaaatac tttctttgcg ggaatgagtt atttattgca      8657
aggtatagat atcacttaac aatgaaagat gcactatatg aaaaaataa ttgtagattt       8717 agataacacc atatctttta atttatcagg aaaatattca catgcaactc caaacaaaaa      8777
actaattgaa aaattgtatg aatataagct taatggtttt tatattgtta tttttacagc      8837
aaggaatatg aggacatata aagaaaatat aggtaagatt aatattcata cattaccagt      8897
tataattgat tggttgaatg aaaatagagt cccttatgat gaggtgattg ttggtaaacc      8957
ttggtgtgga gatgaggggt tttatgttga tgatagagct attcgaccat cagaactttg      9017
caatatgacc ttagaagaga tttctaatat gttagaacag gagaaaaaat gcttctaata      9077
atgtctggtt cctatgttca acaagaatta ggggccgaat ttggttctat tcctccaagc      9137
tttcttcctt tagctaataa acgattattt aagcatcaag tatctttagg gcatgatggt      9197
catgcaatat atctggtttt accggaagat tttgtgtttg acaaacatga ttatgaatgg      9257
ttgcttcgta ataaagtaac aatgatccct gtcgatagta acttgacatt agggcaagcg      9317
atagttaccg catggaattt aataggagat aaagatgaca aaggcttaca attattgttt      9377
ggcgatacac tcttttaaaaa aattcctgca ggggaggaat tagtagcaaa aagtcatcct     9437
gatgaaaatt atcaatgggc cattttttac gaaacagagt taagagccgt cagtagagaa      9497
gataataaaa atgtaatttg tgggtatttt tcttttagaa aaccgaattt ttttattagg      9557
gaattagtta cttcaaaatt tgattttacg gcggcactta aaaagtatca cgacagctat      9617
agtttagcct ctatatacgt gtctgattgg cttgattttg gacatattaa tacatactat      9677
aagtcaaaag tacaatacac aacccagcgt gcatttaatg aattatgcat tacaacaaaa      9737
tccgttatca aatcaagttc aaatgaaagt aaaattgaag ctgaatcaaa atggtttgaa      9797
actattcccg gagaattaaa gatctatact ccaatgttat tggaaccgtt tgatcatatc      9857
agaaagagtt ataagcttga atatttatat aatacgacgt taaatgaatt atttgttttt      9917
tctcgcctac caaataatat tttaacaaat atattaataa gttgtttaga cttcatcgat      9977
ctgtgcaaag aatatcattc aattgatact gacaaaaata tactgcaaga tttatttttat     10037 gaaaaaacga ttgagcgggt tagcaagtac ataacagatt taaatattga tccaaatgca     10097
aaatggaatt ttaataataa tataagcgtt tcaattaatg atattcttta tgatactaat     10157
```

```
aaatttatcc caagtgaact gcaatataaa actattatgc atggcgattt atgctttagt    10217
aatataattt ttaactttag aactggtaga atacaagttt ttgatcccag aggattgaac    10277
cactctggag aaataagtat ttatggtgat tttcgttatg atatagctaa attatcacat    10337
tcaatactag ggctctatga ttggataatt gcaggatatt atataataaa taaaaaaaat    10397
aaaactcata gtattgaatt caaaattaat attgataata aattgtttga aattcaatca    10457
acatttgttt ctataataaa agagaaatat tcaatctccg aaaaatcatt gtatgcgatg    10517
caaatacatt tattttttatc aatgcttccc cttcattccg atgacaaaaa aaggcaagat    10577
gcactatttg ctaatgcatt tagattatat gaaatttta aggaggctgc agtatgatta    10637
taattccaat ggcggggatg agttcgcgtt ttttcaaggc tggatattcc aaaccaaaat    10697
atatgcttga attgaatggt gagtttctat tcgatctatg tttgaaaagt ttcaaattat    10757
attttgagac tgaacatttt gtctttatcc ttagggatgt tttcaatacg aagtcttttg    10817
tattacaaag aatagcatct ttagggatta atagctacac cttgattact cttgataaag    10877
aaactcgggg gcaagcagaa acagtatatt tggctatatc aaaattattt aatatagaac    10937
aaccaatcac tattttttaac attgatacaa ttaggcctaa ttttatattt actaagttcg    10997
aaggggaaaa tgaatgttat attgaagtat ttcgaggaga tggggataac tggtcttttg    11057
ttatgccatc aaatgatgta aaaaatgagg tcattgctac tagcgaaaaa aaacaaattt    11117
ctaacttatg ctgcacagga ttatatcatt tttctacaat taaaaattt atttcagcat    11177 atgaacatta taaaaatcta cctcaagaaa attgggatgc tgggagagtt atatatagcc    11237
ccaatataca attatctaat tagtaatggg atcaaagtgt attatacaga aataaataag    11297
tctgatgtta ttttttgtgg tactcctaga gaatatgaaa atttgcaagg aaaaaaataa    11357
aaattaggtt tggcctaata aatctgataa tttattgtta tcaatgctta atcacatttc    11417 tttgattttta tacacggaat taaatataat ctattatgaa aattgcagtt gctggtgtag    11477
gatatgttgg tatatcaatt gctatattac tttcacaaaa acatgatatt atcgctctcg    11537
atatagatcc taagaaagtt cagttgatta ataaaaaaat atcaccaata tgtgatcctg    11597
aaatacaaaa attttttatct aatagaaaat taaacctata tgctacaaca gaaaaatacg    11657
aagcgtatag agatgctgat tatgttataa tcgcaacacc aaccaattat gatcccatta    11717
ataataactt cgatacactc tcagtagaat cagtagcatg tgacgtacta agtataaatc    11777
ctaatgcaac tatcataatt aaatctacag tccccgtcgg atttactgaa cgactaaaac    11837
gcgatctaaa cacgaataat attatctttt ccccagaatt tttacgtgaa ggtaaagctc    11897
tttatgacaa cctatatcca tctcgtatag ttgtgggaga gagtagcgaa cgagcaagaa    11957
agttcgcaga gcttctcagt gaaggcgcta taaaaaaaga tattccaata ttgttaacgg    12017
atagccctga agctgaagcc attaaacttt ttgcaaatac ttaccttgca atgcggattg    12077
cttatttcaa tgaattggat acttatgcct ccgttcatgg tttagataca aagcaaatta    12137
tagagggtgt tagtttagat cctagaattg gtcaacatta taataatcct tcttttggtt    12197
atggaggtta ctgcttacct aaggatacca agcaatcact cgcaaattat cgtgatgttc    12257
cgcagaactt aatccaggct attgtcgatg ccaatactac ccgaaaagac tttgttgcgg    12317
aggatatatt aagtcgtaaa ccaaaagttg taggaatcta tcgcctcata atgaaagcag    12377
gtagtgataa cttttagagca agtagtattc aaggtgtaat gaaacgactc aaagccaaag    12437
gaattgagat agttgtatat gaacctgtac taaaagagcc ttatttcttt ggttcttatg    12497
ttgagcgtga tattaattct tttaaagaac gtgttgatgt tatagtagcc aatcgccgca    12557
```

-continued

```
cgtcagaatt agaagatgta agtgaaaaag tttatacgcg agatttattt ggtgtcgact    12617
cttgattatg ttcaataatt taaaattttt atggctatta agaaaagtc gatatgtaca    12677
tgctttagct gcaatacaag atgactgccg attttggcag tcaaaacgta tattggcaat    12737
gtacaggctt aatatgtatt ggtcattaca taatcttact gatacaccgt cagattggcg    12797
gtgtaaatta gcaatcaaaa tagctaaaat tgcctgtggt gacataagct taactccgga    12857
attactcatg gagtttaaag acgagttcac agacacacat caaaaagttg agttagcaaa    12917
aaccttagca tcatactctc ctacgttttc attatcatta ttagataatg tcgataattg    12977
tcccttagac ttgtatcagc tcttcaatta agaatcgggt taactcaaaa agctatatca    13037
acactcgctc agattgatgc cagtgatatt gtatattccc ctgatatatt actcttgcaa    13097
aaataatgct ttcagagaaa cggcagaaat ctcgttaaat agacttaacg aatactataa    13157
gtactttggt ttatctccgg tcgcactgac agataactca tctcctttgt caccttgtaa    13217
tattattaca tcgattcctt atcctgccca acgggcccc ctgatttcta ttttaatgac    13277
aacatacaat accggtaggc gggtagaaaa tgcagtaata tcattgctta atcaaacata    13337
ccgttcattt gagctaatta ttgtggatga tgccagcacc gatgatacgc tattccgtct    13397
tcagagatta gcactcaaag atactcgaat aaaaattatt agcctgccac aaaatgttgg    13457
aacatatgct gcaaaacgaa taggcttaat acaggcaaag ggagagtttg tgacatgcca    13517
tgactcagat gactggtccc atcctgaaaa attatttaga cagatatcac ctttattgtt    13577
aaaccctaaa ctaatttgtt cgatttctga ttgggtaagg ttgcaagata atgggatttt    13637
ctatgcgcgt gcggtctatc cactaaaaag actgaatcct tcttctctgt tgtttagaag    13697
agcggatgta ttgcaaaaag cgggcgtttg ggactgtgtt aaaacggggg ctgatagtga    13757
attcattgct cgacttaagc taattttttgg tgattccact gtacatcgta ttaaattgcc    13817
tttgacgcta ggaagccatc gtaccgactc gttaatgaat tcacctacaa caggatatac    13877
atctcaggga atttcaccag atcgccaaaa atattgggat tcctggtcgc gatggcacat    13937
tcaggcgtta agaaataaag aaagtctttta cataggaaat tctgatttca ctaataaaaa    13997
tcgaccattt tctgcgcccg actcaatatt agtagatact aatgccatca aaactgcatt    14057
acaaagtgct catgttaact ttaccagtat ataacttatc actaaatgta taatctataa    14117
tatttatttt aataatttat tgtgttttct aattatagta tgttaatcat ttatttaatg    14177
aatgggagtt tatgaatggt tatgttaatg ccattcattg tgatgttttt ttgatagcat    14237
aatacaatct tttttatctt ttttttatatt ttttatctt gttaaaaatc atctccccat    14297
aataaaccgc attaacctgc gtcttaacca ataaataccc tcgaaacttc ttaaacagtt    14357
tcatattcgg tttaaaatcg gcctgccaga actggtgcaa atgcccttga tacgtcaagc    14417
ctttgatgtc gtacagggca ttgcccatca ctttgagtgg tttgttatga atcagcgcag    14477
agatcc                                                              14483
```

<210> SEQ ID NO 4
<211> LENGTH: 686
<212> TYPE: PRT
<213> ORGANISM: Escherichia coli

<400> SEQUENCE: 4

```
Met Ser Ile Leu Asn Gln Ala Ile Asn Leu Tyr Lys Asn Lys Asn Tyr
1               5                   10                  15

Arg Gln Ala Leu Ser Leu Phe Glu Lys Val Ala Glu Ile Tyr Asp Val
            20                  25                  30
```

```
Ser Trp Val Glu Ala Asn Ile Lys Leu Cys Gln Thr Ala Leu Asn Leu
     35                  40                  45

Ser Glu Val Asp Lys Leu Asn Arg Lys Ala Val Ile Asp Ile Asp
 50                  55                  60

Ala Ala Thr Lys Ile Met Cys Ser Asn Ala Lys Ala Ile Ser Leu Asn
 65                  70                  75                  80

Glu Val Glu Lys Asn Glu Ile Ile Ser Lys Tyr Arg Glu Ile Thr Ala
                 85                  90                  95

Lys Lys Ser Glu Arg Ala Glu Leu Lys Glu Val Glu Pro Ile Pro Leu
                100                 105                 110

Asp Trp Pro Ser Asp Leu Thr Leu Pro Pro Leu Pro Glu Ser Thr Asn
         115                 120                 125

Asp Tyr Val Trp Ala Gly Lys Arg Lys Glu Leu Asp Asp Tyr Pro Arg
         130                 135                 140

Lys Gln Leu Ile Ile Asp Gly Leu Ser Ile Val Ile Pro Thr Tyr Asn
145                 150                 155                 160

Arg Ala Lys Ile Leu Ala Ile Thr Leu Ala Cys Leu Cys Asn Gln Lys
                 165                 170                 175

Thr Ile Tyr Asp Tyr Glu Val Ile Val Ala Asp Asp Gly Ser Lys Glu
                 180                 185                 190

Asn Ile Glu Glu Ile Val Arg Glu Phe Glu Ser Leu Leu Asn Ile Lys
                 195                 200                 205

Tyr Val Arg Gln Lys Asp Tyr Gly Tyr Gln Leu Cys Ala Val Arg Asn
         210                 215                 220

Leu Gly Leu Arg Ala Ala Lys Tyr Asn Tyr Val Ala Ile Leu Asp Cys
225                 230                 235                 240

Asp Met Ala Pro Asn Pro Leu Trp Val Gln Ser Tyr Met Glu Leu Leu
                 245                 250                 255

Ala Val Asp Asp Asn Val Ala Leu Ile Gly Pro Arg Lys Tyr Ile Asp
                 260                 265                 270

Thr Ser Lys His Thr Tyr Leu Asp Phe Leu Ser Gln Lys Ser Leu Ile
         275                 280                 285

Asn Glu Ile Pro Glu Ile Ile Thr Asn Asn Gln Val Ala Gly Lys Val
         290                 295                 300

Glu Gln Asn Lys Ser Val Asp Trp Arg Ile Glu His Phe Lys Asn Thr
305                 310                 315                 320

Asp Asn Leu Arg Leu Cys Asn Thr Pro Phe Arg Phe Ser Gly Gly
                 325                 330                 335

Asn Val Ala Phe Ala Lys Lys Trp Leu Phe Arg Ala Gly Trp Phe Asp
                 340                 345                 350

Glu Glu Phe Thr His Trp Gly Gly Glu Asp Asn Glu Phe Gly Tyr Arg
         355                 360                 365

Leu Tyr Arg Glu Gly Cys Tyr Phe Arg Ser Val Glu Gly Ala Met Ala
         370                 375                 380

Tyr His Gln Glu Pro Pro Gly Lys Glu Asn Glu Thr Asp Arg Ala Ala
385                 390                 395                 400

Gly Lys Asn Ile Thr Val Gln Leu Leu Gln Gln Lys Val Pro Tyr Phe
                 405                 410                 415

Tyr Arg Lys Lys Glu Lys Ile Glu Ser Ala Thr Leu Lys Arg Val Pro
         420                 425                 430

Leu Val Ser Ile Tyr Ile Pro Ala Tyr Asn Cys Ser Lys Tyr Ile Val
         435                 440                 445

Arg Cys Val Glu Ser Ala Leu Asn Gln Thr Ile Thr Asp Leu Glu Val
450                 455                 460
```

-continued

Cys Ile Cys Asp Asp Gly Ser Thr Asp Thr Leu Arg Ile Leu Gln
465                 470                 475                 480

Glu His Tyr Ala Asn His Pro Arg Val Arg Phe Ile Ser Gln Lys Asn
            485                 490                 495

Lys Gly Ile Gly Ser Ala Ser Asn Thr Ala Val Arg Leu Cys Arg Gly
            500                 505                 510

Phe Tyr Ile Gly Gln Leu Asp Ser Asp Phe Leu Glu Pro Asp Ala
        515                 520                 525

Val Glu Leu Cys Leu Asp Glu Phe Arg Lys Asp Leu Ser Leu Ala Cys
530                 535                 540

Val Tyr Thr Thr Asn Arg Asn Ile Asp Arg Glu Gly Asn Leu Ile Ser
545                 550                 555                 560

Asn Gly Tyr Asn Trp Pro Ile Tyr Ser Arg Glu Lys Leu Thr Ser Ala
            565                 570                 575

Met Ile Cys His His Phe Arg Met Phe Thr Ala Arg Ala Trp Asn Leu
            580                 585                 590

Thr Glu Gly Phe Asn Glu Ser Ile Ser Asn Ala Val Asp Tyr Asp Met
        595                 600                 605

Tyr Leu Lys Leu Ser Glu Val Gly Pro Phe Lys His Ile Asn Lys Ile
        610                 615                 620

Cys Tyr Asn Arg Val Leu His Gly Glu Asn Thr Ser Ile Lys Lys Leu
625                 630                 635                 640

Asp Ile Gln Lys Glu Asn His Phe Lys Val Val Asn Glu Ser Leu Ser
            645                 650                 655

Arg Leu Gly Ile Lys Lys Tyr Lys Tyr Ser Pro Leu Thr Asn Leu Asn
            660                 665                 670

Glu Cys Arg Lys Tyr Thr Trp Glu Lys Ile Glu Asn Asp Leu
        675                 680                 685

<210> SEQ ID NO 5
<211> LENGTH: 27
<212> TYPE: DNA
<213> ORGANISM: ARTIFICIAL SEQUENCE
<220> FEATURE:
<223> OTHER INFORMATION: SYNTHETIC DNA

<400> SEQUENCE: 5
acccaacact gctacaacct atatcgg                                      27

<210> SEQ ID NO 6
<211> LENGTH: 30
<212> TYPE: DNA
<213> ORGANISM: ARTIFICIAL SEQUENCE
<220> FEATURE:
<223> OTHER INFORMATION: SYNTHETIC DNA

<400> SEQUENCE: 6
gcgtcttcac caataaatac ccacgaaact                                   30

<210> SEQ ID NO 7
<211> LENGTH: 26
<212> TYPE: DNA
<213> ORGANISM: ARTIFICIAL SEQUENCE
<220> FEATURE:
<223> OTHER INFORMATION: SYNTHETIC DNA

<400> SEQUENCE: 7
cgagaaatac gaacacgctt tggtaa                                       26

```
<210> SEQ ID NO 8
<211> LENGTH: 28
<212> TYPE: DNA
<213> ORGANISM: ARTIFICIAL SEQUENCE
<220> FEATURE:
<223> OTHER INFORMATION: SYNTHETIC DNA

<400> SEQUENCE: 8
actcaatttt ctctttcagc tcttcttg                                          28

<210> SEQ ID NO 9
<211> LENGTH: 30
<212> TYPE: DNA
<213> ORGANISM: ARTIFICIAL SEQUENCE
<220> FEATURE:
<223> OTHER INFORMATION: SYNTHETIC DNA

<400> SEQUENCE: 9
cgggatcccg atgagtattc ttaatcaagc                                        30

<210> SEQ ID NO 10
<211> LENGTH: 30
<212> TYPE: DNA
<213> ORGANISM: ARTIFICIAL SEQUENCE
<220> FEATURE:
<223> OTHER INFORMATION: SYNTHETIC DNA

<400> SEQUENCE: 10
ggaattccgg ccagtctaca tgtttatcac                                        30

<210> SEQ ID NO 11
<211> LENGTH: 108
<212> TYPE: DNA
<213> ORGANISM: ARTIFICIAL SEQUENCE
<220> FEATURE:
<223> OTHER INFORMATION: SYNTHETIC DNA
<220> FEATURE:
<221> NAME/KEY: CDS
<222> LOCATION: (1)..(108)
<223> OTHER INFORMATION:

<400> SEQUENCE: 11 atg ggg ggt tct cat cat cat cat cat cat ggt atg gct agc atg act        48
Met Gly Gly Ser His His His His His His Gly Met Ala Ser Met Thr
1               5                   10                  15 ggt gga cag caa atg ggt cgg gat ctg tac gac gat gac gat aag gat        96
Gly Gly Gln Gln Met Gly Arg Asp Leu Tyr Asp Asp Asp Asp Lys Asp
            20                  25                  30 cga tgg atc ccg                                                        108
Arg Trp Ile Pro
        35

<210> SEQ ID NO 12
<211> LENGTH: 36
<212> TYPE: PRT
<213> ORGANISM: ARTIFICIAL SEQUENCE
<220> FEATURE:
<223> OTHER INFORMATION: SYNTHETIC DNA

<400> SEQUENCE: 12

Met Gly Gly Ser His His His His His His Gly Met Ala Ser Met Thr
1               5                   10                  15

Gly Gly Gln Gln Met Gly Arg Asp Leu Tyr Asp Asp Asp Asp Lys Asp
            20                  25                  30

Arg Trp Ile Pro
        35
```